(12) United States Patent
Farha et al.

(10) Patent No.: US 8,470,075 B2
(45) Date of Patent: *Jun. 25, 2013

(54) TETRATOPIC PHENYL COMPOUNDS, RELATED METAL-ORGANIC FRAMEWORK MATERIALS AND POST-ASSEMBLY ELABORATION

(75) Inventors: Omar K. Farha, Morton Grove, IL (US); Joseph T. Hupp, Northfield, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/608,940

(22) Filed: Sep. 10, 2012

(65) Prior Publication Data

US 2013/0061752 A1    Mar. 14, 2013

Related U.S. Application Data

(63) Continuation of application No. 12/578,357, filed on Oct. 13, 2009, now Pat. No. 8,262,775.

(60) Provisional application No. 61/195,876, filed on Oct. 10, 2008.

(51) Int. Cl.
| | |
|---|---|
| *B01D 53/02* | (2006.01) |
| *C07C 63/42* | (2006.01) |
| *C07F 3/06* | (2006.01) |
| *C07F 15/00* | (2006.01) |

(52) U.S. Cl.
USPC .............. 95/139; 95/45; 95/90; 96/4; 96/108; 562/469; 562/488; 556/118; 546/2; 502/4; 502/400

(58) Field of Classification Search
USPC .............. 95/45, 90, 116, 139, 900; 96/4, 108; 562/469, 488; 556/118; 546/2; 502/4, 400
See application file for complete search history.

(56) References Cited

U.S. PATENT DOCUMENTS

| | | | |
|---|---|---|---|
| 3,384,658 | A | 5/1968 | McCracken et al. |
| 4,339,595 | A | 7/1982 | Udovich et al. |
| 4,883,898 | A | 11/1989 | Yang |
| 6,566,548 | B1 | 5/2003 | Abe et al. |
| 7,253,004 | B2 | 8/2007 | Vossmeyer et al. |
| 8,262,775 | B2 * | 9/2012 | Farha et al. ............... 95/139 |
| 2005/0025993 | A1 | 2/2005 | Thompson et al. |
| 2006/0287190 | A1 | 12/2006 | Eddaoudi et al. |
| 2011/0274713 | A1 | 11/2011 | Burn et al. |

OTHER PUBLICATIONS

Ferey G. Hybrid porous solids: past, present and future. Chem. Soc. Rev. 2008, 37, pp. 191-214.

Wang, Xi-Sen et al., "Metal-Organic Frameworks Based on Double-Bond-Coupled Di-Isophthalate Linkers with High Hydrogen and Methane Uptakes", Chemical Materials, Apr. 2008, vol. 20, pp. 3145-3152.

(Continued)

*Primary Examiner* — Jason M Greene
(74) *Attorney, Agent, or Firm* — The Marbury Law Group PLLC

(57) ABSTRACT

Disclosed are tetratopic carboxylic acid phenyl for use in metal-organic framework compounds. These compounds are useful in catalysis, gas storage, sensing, biological imaging, drug delivery and gas adsorption separation.

13 Claims, 32 Drawing Sheets

OTHER PUBLICATIONS

Ma, Bao-Qing et al., "Microporous Pillared Paddle-Wheel Frameworks Based on Mixed-Ligand Coordination of Zinc Ions", Inorganic Chemistry Communication, 2005, vol. 44, pp. 4912-4914.

Mavrandonakis A; Tylianakis E; Stubos AK; Froudakis GE. Why Li Doping in MOFs Enhances H2 Storage Capacity? A Multi-scale Theoretical Study. J. Phys. Chem. C 2008, vol. 112, No. 18, pp. 7290-7294.

Yang Q; Xue C; Zhong C; Chen J-F. Molecular Simulation of Separation of CO2 from Flue Gases in Cu-BTC Metal-Organic Framework. AIChE Journal, Nov. 2007, vol. 53 No. 11, pp. 2832-2840.

Snurr RQ; Hupp JT; Nguyen ST. Prospects for Nanoporous Metal-Organic Materials in Advanced Separations Processes. AIChE Journal, Jun. 2004, vol. 50, No. 6, pp. 1090-1095.

Kolb HC; Finn MG; Sharpless KB. Click Chemistry: Diverse Chemical Function from a Few Good Reactions. Angew. Chem. Int. Ed. 2001, 40, pp. 2004-2021.

Cho Sh; Ma B; Nguyen SBT; Hupp JT; Albrecht-Schmitt TE. A metal-organic framework material that functions as an enantioselective catalyst for olefin epoxidation. Chem. Commun., 2006, pp. 2563-2565.

Jian-Rong Li et al: "Hydrogen-Bonded Supramolecular Architectures of Organic Salts Based on Aromatic Tetracarboxylic Acids and Amines." Growth&Design 2006, vol. 6, No. 11, pp. 2493-2500.

Xi-Sen Wang: "Metal-Organic Frameworks Based on Double-Bond-Coupled Di-Isophthalate Linkers with High Hydrogen and Methane Uptakes." Chem. Mater. 2008 (published on Web Apr. 15, 2008), 20, pp. 3145-3152. See Scheme 1 and Scheme 2.

Bae Y-S; Mulfort KL; Frost H; Ryan P; Punnathanam S; Broadbelt LJ; Hupp JT; Snurr RQ. Separation of CO2 from CH4 Using Mixed Ligand Metal-Organic Frameworks. Langmuir, 2008, vol. 24, No. 16, pp. 8592-8598.

Seo, JS; Whang D; Lee H; Jun Si; Oh J; Jeon YJ; Kim K. A homochiral metal-organic porous material for enantioselective separation and catalysis. Nature, vol. 404, Apr. 27, 2000, pp. 982-986.

Cho, So-Hye; Gadzikwa, Tendai; Emberger, Gloria A.; Snurr, Randall Q.; Nguyen, Sonbinh T.; Hupp, Joseph T Synthesis of [bis(pyridine)salen]ZnII-based coordination polymers and their application in enantioselective separations. PMSE Preprints (2007), 97 95-96. CODEN: PPMRA9 ISSN:1550-6703. CAN 149:416192 AN 2007:854501 CAPLUS, full text unavailable.

Blomqvist A; Ara jo CM; Srepusharawoot, P; Ahuja R. Li-decorated metal-organic framework 5: A route to achieving a suitable hydrogen storage medium. PNAS, Dec. 18, 2007, vol. 104, No. 51, pp. 20173-20176.

Chui S S-Y; Lo S M-F; Charmant JPH; Orpen AG; Williams ID. A Chemically Functionalizable Nanoporous Material [Cu3(TMA)2(H2O3)n. www.sciencemag.org, Science, vol. 283, Feb. 19, 1999, pp. 1148-1150.

Eddaoudi M; Kim J; Rosi N; Vodak D; Wachter J; O'Keeffe M; Yaghi OM. Systematic Design of Pore Size and Functionality in Isoreticular MOFs and Their Application in Methane Storage. www.sciencemag.org, Science, vol. 295, Jan. 18, 2002, pp. 469-472.

Challa, SR; Sholl DS; Johnson JK. Adsorption and separation of hydrogen isotopes in carbon nanotubes: Multicomponent grand canonical Monte Carlo simulations. J. Chem. Phys., vol. 116, No. 2, Jan. 8, 2002, pp. 814-824.

Goj, A; Sholl DS; Akten ED; Kohen D. Atomistic Simulations of CO2 and N2 Adsorption in Silica Zeolites: The Impact of Pore Size and Shape. J. Phys. Chem. B., 2002, vol. 106, No. 33, pp. 8367-8375.

Dalach P; Frost H; Snurr RQ; Ellis DE. Enhanced Hydrogen Uptake and the Electronic Structure of Lithium-Doped Metal-Organic Frameworks. J. Phys. Chem. C, 2008, vol. 112, No. 25, pp. 9278-9284.

Yang Q; Zhong C. Molecular Simulation of Carbon Dioxide/Methane/Hydrogen Mixture Adsorption in Metal-Organic Framework. J. Phys. Chem. B, 2006, vol. 110, No. 36, pp. 17776-17783.

Frost H; Duren T; Snurr RQ. Effects of Surface Area, Free Volume, and Heat of Adsorption on Hydrogen Uptake in Metal-Organic Frameworks. J. Phys. Chem. B, 2006, vol. 110, No. 19, pp. 9565-9570.

Babarao R; Hu Z; Jiang J; Chempath S; Sandler SI. Storage and Separation of CO2 and CH4 in Silicalite, C168, Schwarzite, and IRMOF-1: A Comparative Study from Monte Carlo Simulation. Langmuir, 2007, vol. 23, No. 2, pp. 659-666.

Dinca M; Dailly A; Liu Y; Brown CM; Neumann DA; Long JR. Hydrogen Storage in a Microporous Metal-Organic Framework with Exposed Mn2+ Coordination Sites. J. Am. Chem. Soc., 2006, vol. 128, No. 51, pp. 16876-16883.

Kaye SS; Long Jr. Matrix Isolation Chemistry in a Porous Metal-Organic Framework: Photochemical Substitutions of N2 and H2 in Zn4O[.eta.6-1,4-Benzenedicarboxylate)Cr(CO)3]3. J. Am. Chem. Soc., 2008, vol. 130, No. 3, pp. 806-807.

Nouar F; Eubank Jr; Bousquet T; Wojtas L; Zaworotko MJ; Eddaoudi M. Supermolecular Building Blocks (SBBs) for the Design and Synthesis of Highly Porous Metal-Organic Frameworks. J. Am. Chem. Soc., 2008, vol. 130, No. 6, pp. 1833-1835.

Tanabe KK; Wang Z; Cohen, SM. Systematic Functionalization of a Metal-Organic Framework via a Postsynthetic Modification Approach. J. Am. Chem. Soc. 2008, vol. 130, No. 26, 2008, pp. 8508-8517.

Collins DJ; Zhou H-C. Hydrogen storage in metal-organic frameworks. J. Mater. Chem., 2007, 17, pp. 3154-3160.

Spek, AL. Single-crystal structure validation with the program PLANTON. J. Appl. Cryst. (2003), 36, pp. 7-13.

Han SS; Goddard III WA. Lithium-Doped Metal-Organic Frameworks for Reversible H2 Storage at Ambient Temperature. J. Am. Chem. Soc., vol. 129, No. 27, 2007, pp. 8422-8423.

Mulfort KL; Hupp JT. Chemical Reduction of Metal-Organic Framework Materials as a Method to Enhance Gas Uptake and Binding. J. Am. Chem. Soc. 2007, vol. 129, No. 31, pp. 9604-9605.

Wang Z; Cohen SM. Postsynthetic Covalent Modification of a Neutral Metal-Organic Framework. J. Am. Chem. Soc. 2007, vol. 129, No. 41, pp. 12368-12369.

Farha OK; Spokoyny AM; Mulfort KL; Hawthorne MF; Mirkin CA; Hupp JT. Synthesis and Hydrogen Sorption Properties of Carborane Based Metal-Organic Framework Materials. J. Am. Chem. Soc. 2007, vol. 29, No. 42, pp. 12680-12681.

Fujita M; Kwon YJ; Washizu S; Ogura K. Preparation, Clathration Ability, and Catalysis of a Two-Dimensional Square Network Material Composed of Cadmium(II) and 4,4'-Bipyridine. J.Am. Chem. Soc. 1994, vol. 116, No. 3, pp. 1151-1152.

Rieter WJ; Taylor KM; An H; Lin W; Lin W. Nanoscale Metal-Organic Frameworks as Potential Multimodal Contrast Enhancing Agents. J. Am. Chem. Soc., vol. 128, No. 28, 2006, pp. 9024-9025.

Mulfort KL; Hupp JT. Alkali Metal Cation Effects on Hydrogen Uptake and Binding in Metal-Organic Frameworks. Inorganic Chemistry, vol. 47, No. 18, 2008, pp. 7936-7938.

Sawaki T; Aoyama Y. Immobilization of a Soluble Metal Complex in an Organic Network. Remarkable Catalytic Performance of a Porous Dialkoxyzirconium Polyphenoxide as a Functional Organic Zeolite Analogue. J. Am. Chem. Soc. 1999, 121, pp. 4793-4798.

Hu A; Ngo HL; Lin W. Chiral Porous Hybrid Solids for Practical Heterogeneous Asymmetric Hydrogenation of Aromatic Ketones. J. Am. Chem. Soc., vol. 125, No. 38, 2003, pp. 11490-11491.

Wu C-D; Hu A; Zhang L; Lin W. A Homochiral Porous Metal-Organic Framework for Highly Enantioselective Heterogeneous Asymmetric Catalysis. J. Am. Chem. Soc., vol. 127, No. 25, 2005, pp. 8940-8941.

Lee EY; Jang SY; Suh MP. Multifunctionality and Crystal Dynamics of a Highly Stable, Porous Metal—Organic Framework. [Zn4O(NTB)2]. J. Am. Chem. Soc., vol. 127, No. 17, 2005, pp. 6374-6381.

Dinca M; Long Jr. Strong H2 Binding and Selective Gas Adsorption within the Microporous Coordination Solid Mg3 (O2C-C10H6-CO2)3. J. Am. Chem. Soc., vol. 127, No. 26, 2005, pp. 9376-9377.

Gadzikwa T; Zeng B-S; Hupp JT; Nguyen SBT. Ligand-elaboration as a strategy for engendering structural diversity in porous metal-organic framework compounds. Chem. Commun., 2008, pp. 3672-3674.

Bae Y-S; Farha OK; Spokoyny AM; Mirkin CA; Hupp JT; Snurr RP. Carborane-based metal-organic frameworks as highly selective sorbents for CO2 over methane. Chem. Commun., 2008, pp. 4135-4137.

Gadzikwa T; Lu G; Stern CL; Wilson SR; Hupp JT; Nguyen SBT. Covalent surface modification of a metal-organic framework; selective surface engineering via CuI-catalyzed Huisgen cycloaddition. Chem. Commun., 2008, pp. 5493-5495.

Czepirski L; Jagiello J. Virial-Type Thermal Equation of Gas-Solid Adsorption. Chemical Engineering Science, vol. 44, No. 4, pp. 797-801, 1989.

Kesanli B; Lin W. Chiral porous coordination networks: rational design and applications in enantioselective processes. Coordination Chemistry Reviews, 246 (2003) pp. 305-326.

Zhao D; Yuan D; Zhou H-C. The current status of hydrogen storage in metal-organic frameworks. Energy Environ. Sci., 2008, 1, pp. 222-235.

Chen B; Ockwig NW; Millward AR; Contreras DS; Yaghi OM. High H2 Adsorption in a Microporous Metal-Organic Framework with Open Metal Sites. Angew. Chem. Int. Ed. 2005, 44, pp. 4745-4749.

Latroche M; Surble S; Serre C; Mellot-Draznieks C; Llewellyn PL; Lee J-H; Chang J-S; Jhung SH; Ferey G. Hydrogen Storage in the Giant-Pore Metal-Organic Frameworks MIL-100 and MIL-101. Angew. Chem. Int. Ed. 2006, 45, pp. 8227-8231.

Hwang YK; Hong D-Y; Chang J-S; Jhung SH; Seo Y-K; Kim J; Vimont A; Daturi M; Serre C; Ferey G. Amine Grafting on Coordinatively Unsaturated Metal Centers of MOFs: Consequences for Catalysis and Metal Encapsulation. Angew. Chem. Int. Ed, 2008, 47, pp. 4144-4148.

Wang Z; Cohen SM. Tandem Modification of Metal-Organic Frameworks by a Postsynthetic Approach. Angew. Chem. Int. Ed. 2008, 47, pp. 4699-4702.

Horcajada P; Serre C; Vallet-Regi M; Sebban M; Taulelle F; Ferey G. Metal-Organic Frameworks as Efficient Materials for Drug Delivery. Angew. Chem. Int. Ed. 2006, 45, pp. 5974-5978.

* cited by examiner

R' = COOH, SO$_3$, PO(OH)$_3$, COOM (M=Li, Na, CH$_3$, CH$_2$CH$_3$, etc)
R = H, F, Br, I, CH$_3$, COOH, etc
R" = H, F, Br, I, CH$_3$, COOH, etc R' = COOH, SO$_3$, PO(OH)$_3$, COOM (M=Li, Na, CH$_3$, CH$_2$CH$_3$, etc)
R = H, F, Br, I, CH$_3$, COOH, etc
R" = H, F, Br, I, CH$_3$, COOH, etc
n = 1, 2, etc R' = COOH, SO$_3$, PO(OH)$_3$, COOM (M=Li, Na, CH$_3$, CH$_2$CH$_3$,etc)
R = H, F, Br, I, CH$_3$, COOH, etc
R" = H, F, Br, I, CH$_3$, COOH, etc δ (ppm)

TETRATOPIC PHENYL COMPOUNDS, RELATED METAL-ORGANIC FRAMEWORK MATERIALS AND POST-ASSEMBLY ELABORATION

This application is a continuation of and claims priority benefit of application Ser. No. 12/578,357 filed on Oct. 13, 2009 and issued as U.S. Pat. No. 8,262,775 on Sep. 11, 2012 and application Ser. No. 61/195,876 filed Oct. 10, 2008, each of which is incorporated herein by reference in its entirety.

This invention was made with government support under grant no. DE-FG02-01ER15244 awarded by the Department of Energy. The government has certain rights in the invention.

FIELD OF THE INVENTION

The present invention relates to tetracarboxylic acid and related species. These compounds can be used in a crystalline metal-organic framework. More specifically, the invention relates to a tetratopic phenyl and related metal-organic framework compounds. Such metal-organic framework compounds of the present invention are suitably used in catalysis, gas storage, sensing, biological imaging, drug delivery and gas adsorption separation.

BACKGROUND OF THE INVENTION

Crystalline metal-organic frameworks (MOFs) comprise a rapidly growing class of permanently microporous materials.[1] They are characterized by low densities, high internal surface areas, and uniformly sized pores and channels. These properties point to a broad range of potential applications, including chemical separations,[2] catalysis,[3] gas storage and release,[4] biological imaging,[5] and drug delivery.[6] Many of these applications require comparatively large cavities. On the other hand, MOF syntheses typically produce catenated structures, thereby reducing cavity size, increasing density, diminishing vapor-uptake capacity and diminishing gravimetric surface area (See FIG. 1). In most cases non-catenated MOFs are desired, but experimentally catenated structures are often obtained.

Optimal performance in applications depends upon the ability to obtain MOFs having: a) cavities and pores of optimal size, shape, and/or chirality, and b) interior and/or exterior surfaces of suitable chemical composition. Systematic (i.e. predictable) tunability of pore size and, to some extent, surface chemical composition, has indeed been nicely demonstrated for certain families of MOFs.[7] For others, however, even minor changes in synthesis conditions or strut composition can lead—seemingly unpredictably—to significant differences in cavity-defining metal-node/organic-strut coordination and/or degree of framework catenation.[8] Additionally, certain desirable functional groups may be difficult to incorporate directly into MOFs, either due to thermal instability under materials synthesis conditions[9] or because of competitive reaction with intended framework components. Together, these complications can make direct assembly of MOFs that are optimal for specific applications particularly challenging.

An emerging alternative design strategy is to construct robust precursor MOFs and then chemically elaborate their internal and/or external surfaces to impart desired properties. While only a handful of examples has thus far been reported,[3f,4e,10] it is clear that the strategy is a powerful one. For example, Wu and co-workers added highly catalytic Ti(IV) sites to the chiral dinapthol-based struts of a pre-formed MOF and subsequently used the MOF to facilitate the enantioselective addition of $ZnEt_2$ to aromatic aldehydes.[3f] Kaye and Long[10e] photochemically attached $Cr(CO)_3$ to a benzene dicarboxylate strut in $\eta^6$ fashion. Wang and Cohen[10a] were able to modify IRMOF-3 post-synthetically by reacting pendant amines with anhydrides; they subsequently demonstrated that modification could alter the affinities of a simple cubic MOF for various guest molecules.[10c] Various other efforts have been directed to: a) the introduction of charge-compensating alkali metal cations (potential $H_2$ binding sites[11]) via strut reduction,[4e,10g] b) surface tailoring of non-porous metallo-salen MOFs via reversible coordination of salen metal sites with chiral ligands and subsequent use of the modified MOFs to accomplish partial separation of the R and S forms of 2-phenylethylalcoho[12] and c) "click" based modification[13] of alkyne-bearing struts to impart hydrophilicity.[10f]

SUMMARY OF THE INVENTION

The present invention can be directed to a class of metal-organic framework building blocks comprising tetratopic carboxylic acids and related compounds. Such a building block can feature a phenyl ring core, substituted at the 1-, 2-, 4-, and 5-positions with substituted phenyl ring spacers. The carboxylic acids, used to bind metal ion or cluster nodes, can be located at the 4-postion of each phenyl ring spacer, although other positioning can be employed.

Without limitation, this invention can be directed to a broad range of tetracarboxylic acid and related species; e.g., 4',5'-bis(4-carboxyphenyl)-[1,1':2',1"-terphenyl]-4,4"-dicarboxylic acid (named according to ChemDraw Ultra 12.0; other names include 4,4',4",4'''-benzene-1,2,4,5-tetrayl-tetrabenzoic acid or 1,2,4,5-tetrakis(4-carboxyphenyl)benzene, 2. (See, e.g., scheme 1, below; and, more generally and without limitation, structural variations of the sort provided in FIGS. 2A -2C.) Without limitation, deprotonated 2 would, as: a) an unusually shaped molecule, resist formation of catenated MOFs, b) a tetra-topic building block, produce robust frameworks, and c) a nonplanar moiety, potentially produce a 3D framework. Such characteristics can favor the formation of comparatively large cavities which can be shown experimentally. Additionally, representative of various other embodiments of this invention, 2 can readily form more complex, non-catenated MOF materials when combined with other candidate organic struts. In accordance with this invention, various other compounds can be prepared using synthetic techniques of the sort described herein, or straightforward modifications thereof, as would be understood by those skilled in the art made aware of this invention. (see, e.g., FIGS. 3, 4, and 5).

Nearly all approaches taken in the prior art entail elaboration of struts of intact framework compounds[14] (and, see the recent report by Hwang et al.[15]). In contrast thereto, this invention involves MOF cavity modification via activation[4f,16] and elaboration of framework nodes. As shown below, cavity modification can affect material ability to sorb molecular hydrogen.

With respect to one non-limiting embodiment, a robust, non-catenated, and permanently microporous metal-organic framework (MOF) material has been synthesized by combining a new nonplanar ligand, 4,4',4'',4'''-benzene-1,2,4,5-tetrayl-tetrabenzoic acid, with a Zn(II) source under solvothermal conditions. The new material features cavities that are readily modified via activation and functionalization of framework nodes (as opposed to struts). Preliminary investigation of the "empty cavity" version of the material and six cavity-modified versions reveals that modification can substantially modulate the MOF's internal surface area, pore volume, and ability to sorb molecular hydrogen. Regardless, any metal source can be selected that would favor the formation of a comparatively large cavity to produce a MOF with a broad range of potential applications. Accordingly, as would be understood in the art, a metal site component can, without limitation, comprise another metal ion capable of coordination chemistry comparable to or available through Zn(II).

Other objectives, features, benefits and advantages of the present invention will be apparent from this summary and its descriptions of certain embodiments of such MOF compounds, and will be readily apparent to those skilled in the art having knowledge of the synthetic techniques described therewith. Such objectives, features, benefits and advantages will be apparent from the above as taken into conjunction with the accompanying examples, data, figures and all reasonable inferences to be drawn therefrom.

Accordingly, the invention can also be directed to a gas adsorption separation process characterized by adsorption separation of components in a gas by contacting the gas with a MOF of the invention. Such a process can be employed to reduce the emission of gases from industrial processes. Specifically, the MOFs of the instant invention can be used for the adsorption of such gases as, for example, $H_2$, $CO_2$, $N_2$ and $CH_4$. In a certain embodiment, the MOF of the invention acts as an adsorbent with high selectivity for one or more gases.

DETAILED DESCRIPTION OF CERTAIN EMBODIMENTS

The invention relates to a new tetracarboxylic acid species (4,4',4'',4'''-benzene-1,2,4,5-tetrayl-tetrabenzoic acid, 2), and salts thereof, as shown in Scheme 1. A deprotonated 2 was found to be a) an unusually shaped molecule, resisting formation of catenated MOFs, b) a tetra-topic building block, producing robust frameworks, and c) a nonplanar moiety, producing a 3D framework. These three characteristics favor the formation of comparatively large cavities, a desirable feature for post-assembly functionalization.

Scheme 1.

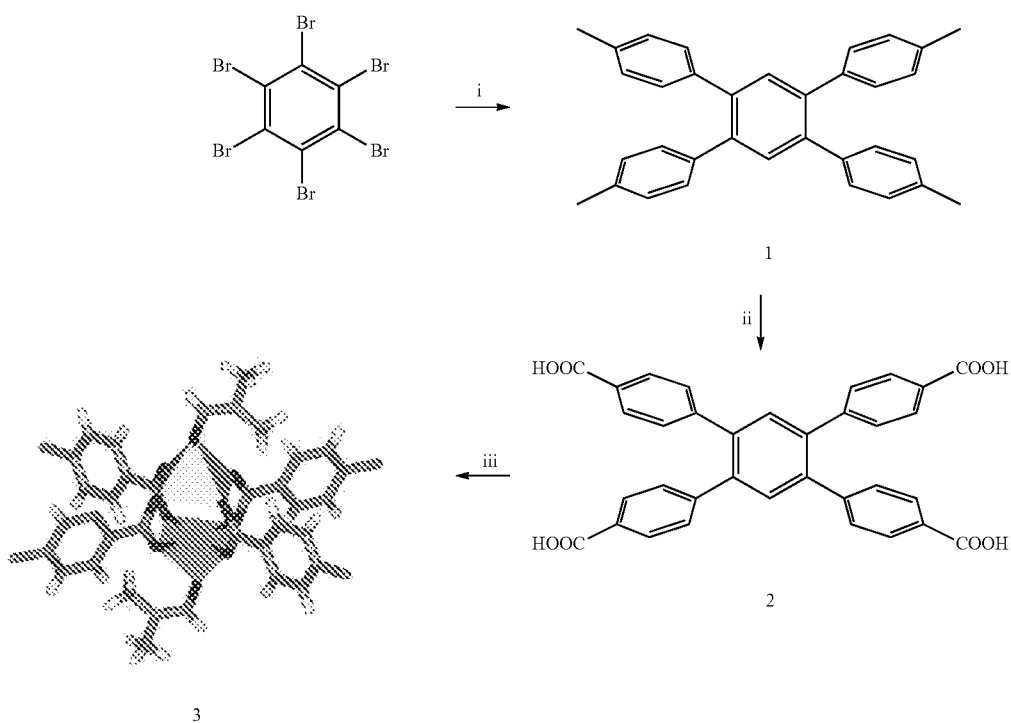

Figure 6:
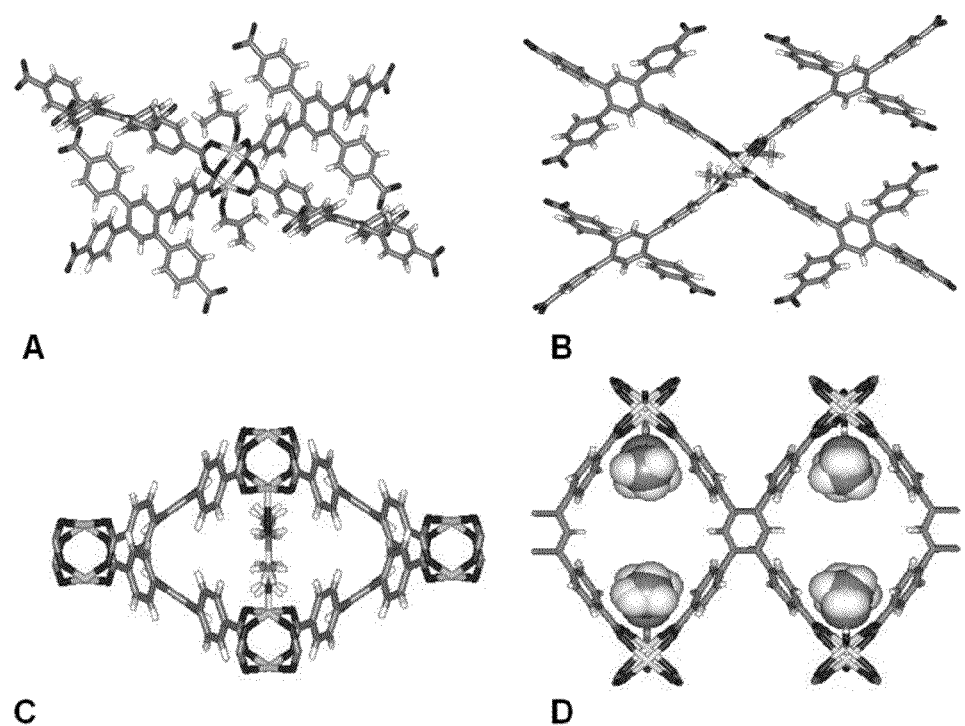
FIG. 6 depicts crystallographically derived MOF 3: (A) structure of 3, (B) topology and connectivity of 3, (C) ac-plane, looking down b-channels, and (D) ab-plane, looking down c-channels (coordinated DMF molecules are shown in space-filling fashion, while non-coordinated solvent molecules (disordered) are omitted from the structure representations).
Figure 7:
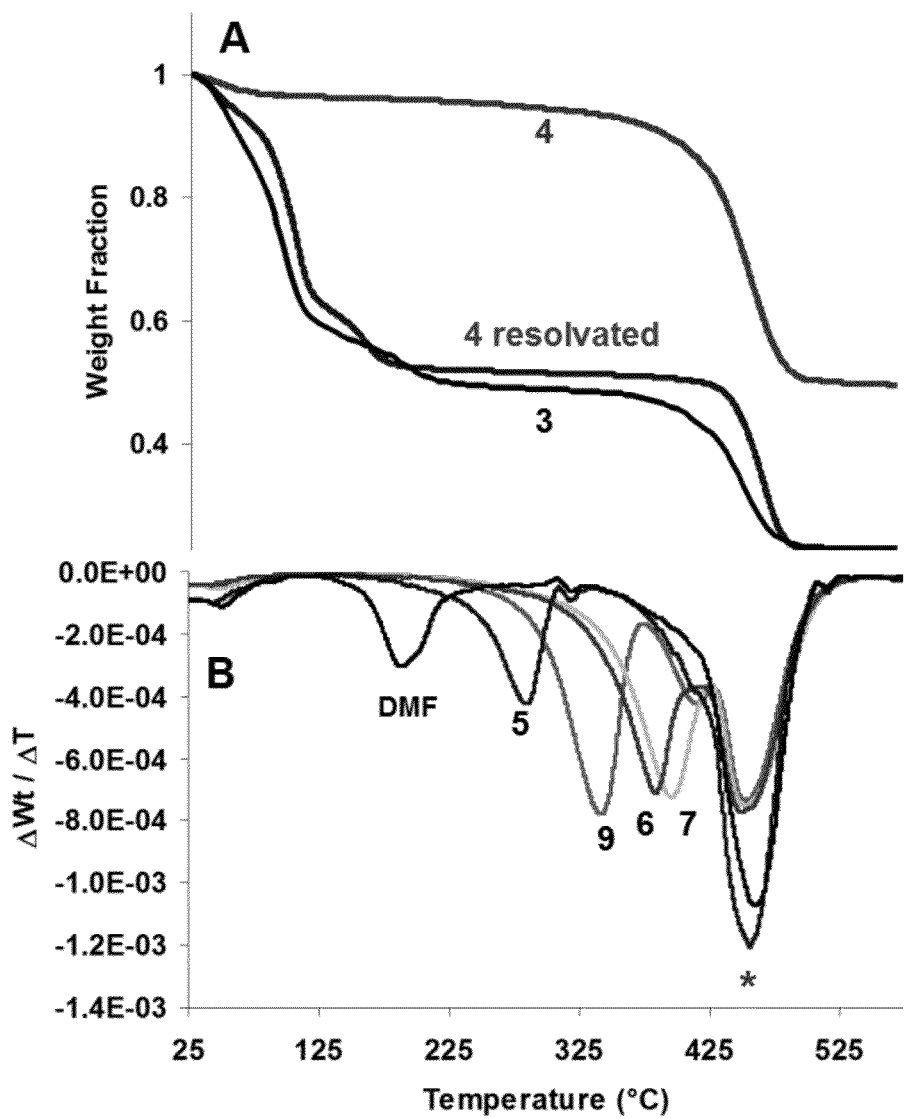
FIG. 7 depicts (A) thermogravimetric analyses of 3 as synthesized (black), 4 (red), and 4 resolvated (blue); and (B) first-derivative thermogravimetric analyses plots for solvent-evacuated, py-R-modified MOFs. For presentation clarity, curve for MOF modified with 8 is omitted.

Added reagents: i) p-tolylmagnesium bromide/THF, ii) HNO₃/H₂O, iii) Zn(NO₃)₂ 6H₂O/DMF Solvothermal reaction of 2 and Zn(NO$_3$)$_2$·6H$_2$O in DMF at 80° C. for 24 hours afforded in high yield a MOF (3) having the framework formula [Zn$_2$(2)(DMF)$_2$]$_n$ [DMF=dimethylform-amide] (Scheme 1, FIGS. 6 and 7), wherein n can range from about 10—about 100, and preferably from about 25—about 100. X-ray analysis of a single crystal of 3 revealed a non-catenated structure in which the framework nodes consist of Zn(II)$_2$ units coordinated by the carboxylates of 2 in paddlewheel fashion. Notably, the strut twists sufficiently to create a true 3D, rather than layered-2D, framework Importantly, the axial sites of the Zn(II)$_2$ units are ligated by solvent molecules.

Thermogravimetric analysis (TGA) of 3 revealed mass losses at about 100° C. and 175° C., assigned to free and coordinated DMF, respectively; no further mass loss occurs until 425° C. (FIG. 7A). Heating 3 under vacuum at 100° C. allows for selective removal of non-coordinated DMF, while heating under vacuum at 150° C. removes all solvent molecules. The partially and fully evacuated MOFs are designated, respectively, 3' and 4. Void volumes from PLATON[17] for 3' and 4 are 53 and 65%, respectively. Follow up TGA experiments (FIG. 7A) show that 4 can be fully resolvated, while powder X-ray diffraction (PXRD) shows that the resolvated form retains crystallinity.

Figure 8:
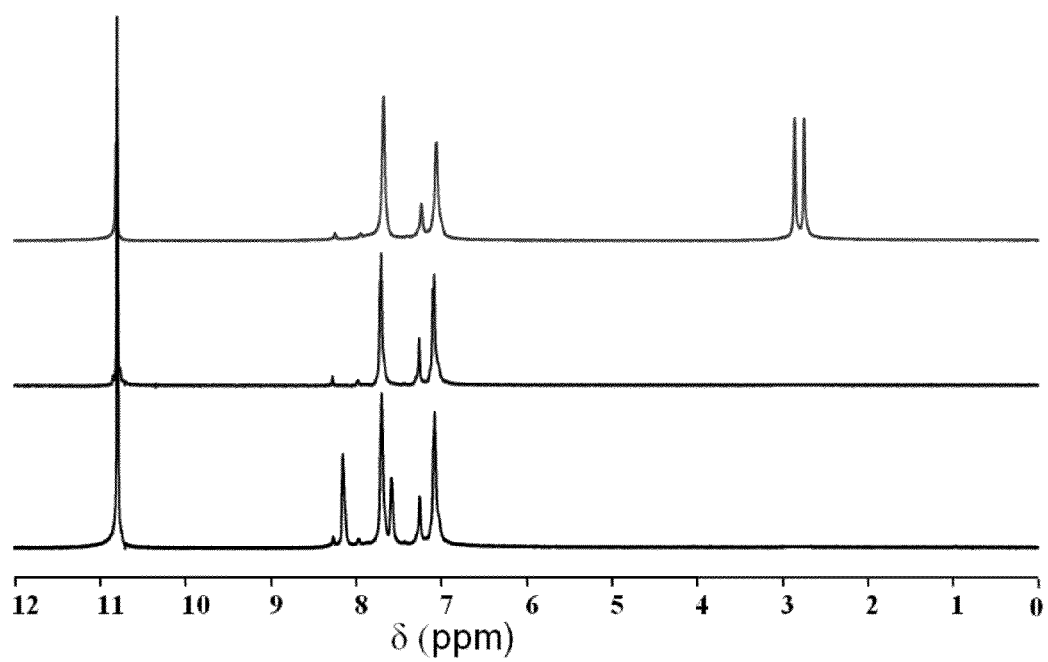
FIG. 8 shows the $^1$H NMR of dissolved 3' (top), 4 (middle), and 4+5 (bottom).
Figure 9:
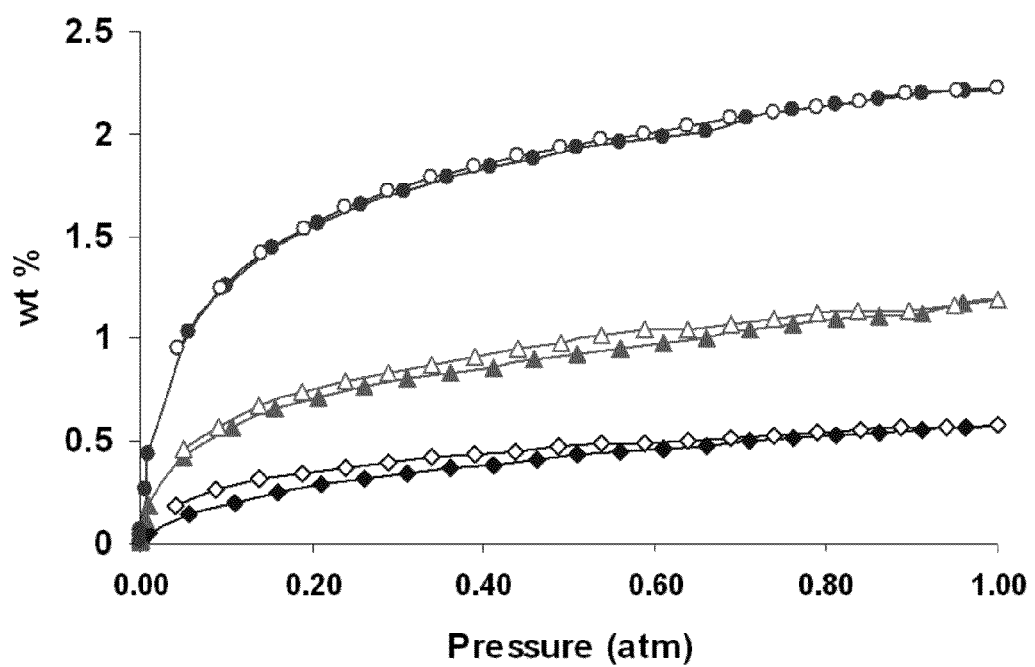
FIG. 9 depicts the isotherms for uptake of $H_2$ at 77 K and 1 atm. by: 4+9 (bottom), 3' (middle), and 4 (top).

The thermal lability of coordinated DMF should permit its replacement by other ligands. Samples of 3 were converted to 4 and immersed for 24 hours in CH$_2$Cl$_2$ solutions of each of several candidate pyridine ligands (py-R, 5-9). Following an extensive washing, soaking, and drying protocol designed to remove solvent and free ligands, each of the putative py-R-modified MOFs was dissolved in D$_2$SO$_4$/D$_2$O. $^1$H NMR measurements established the retention of py-R ligands (see example in FIG. 8).

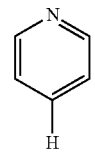

5

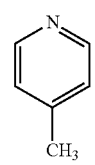

6

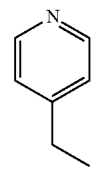

7

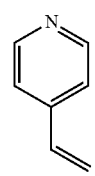

8

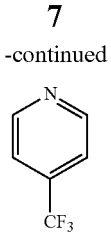

In each case, proton peak integrations were consistent with complete derivatization of Zn(II) nodes and formation of the desired cavity-modified species, $[Zn_2(2)(py-R)_2]_n$, wherein n is about 10—about 100, and preferably about 25—about 100. TGA measurements of rinsed and dried samples provided compelling support for coordinative (as opposed to sorptive) binding of the various py-R. As shown in FIG. 7B, the pyridines bind to the zinc sites more strongly than does DMF, with temperatures for dissociation ranging from ~260 to ~375° C. Finally, TGA measurements with resolvated samples established that the modified MOFs retain high porosities.

Figure 22:
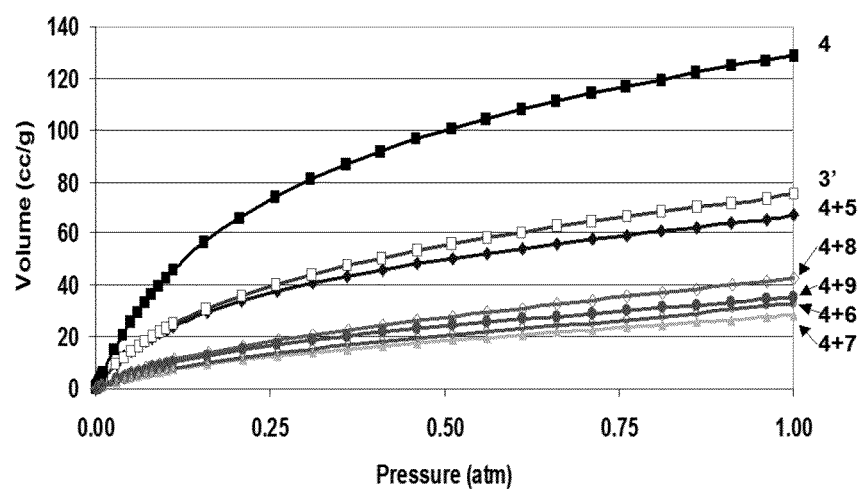
FIG. 22 depicts $CO_2$ isotherms at 273K. Desorption curves are omitted for clarity.
Figure 23:
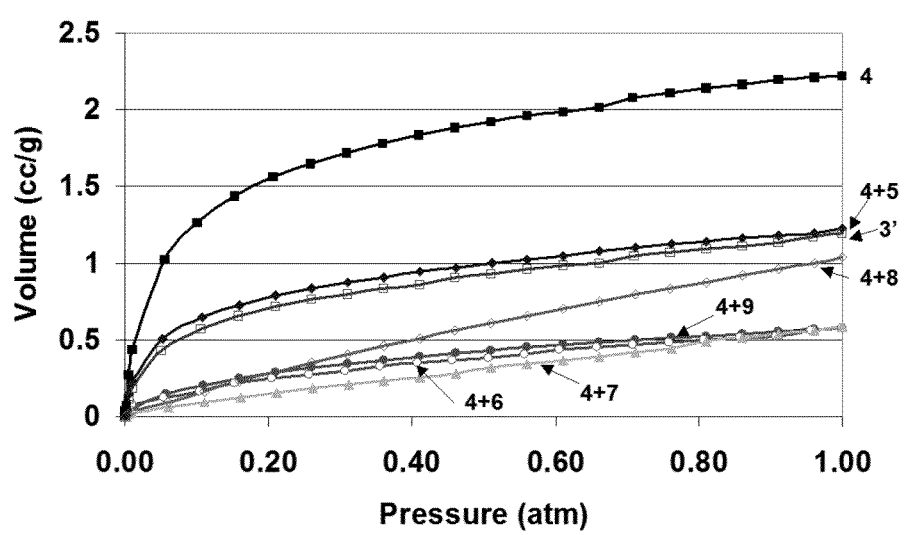
FIG. 23 depicts $H_2$ isotherms at 77K. Desorption curves are omitted for clarity.
Figure 24:
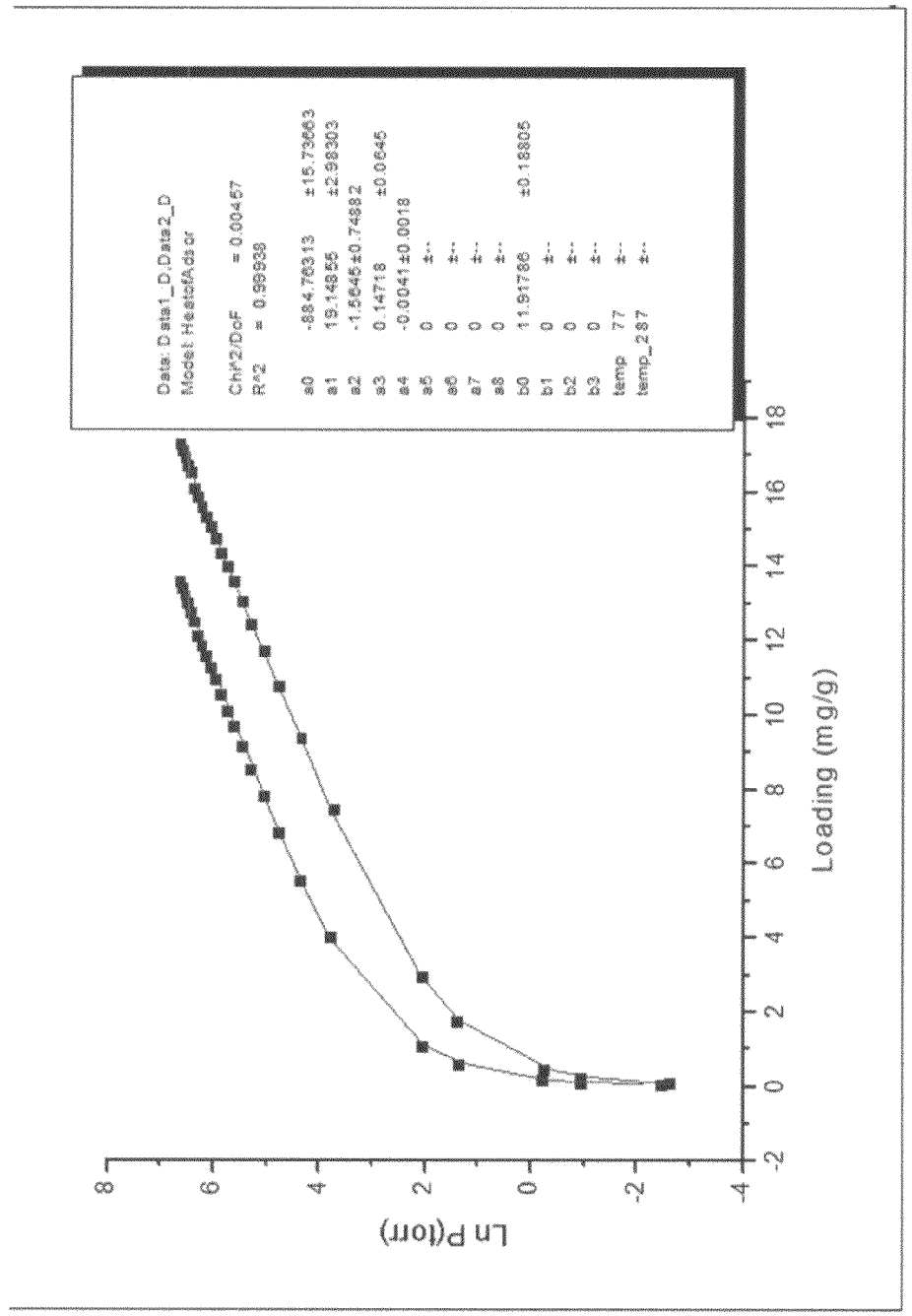
FIG. 24 depicts $H_2$ isotherms at 77K and 87K (black squares) and virial equation fits (red line) for 3' (I).
Figure 25:
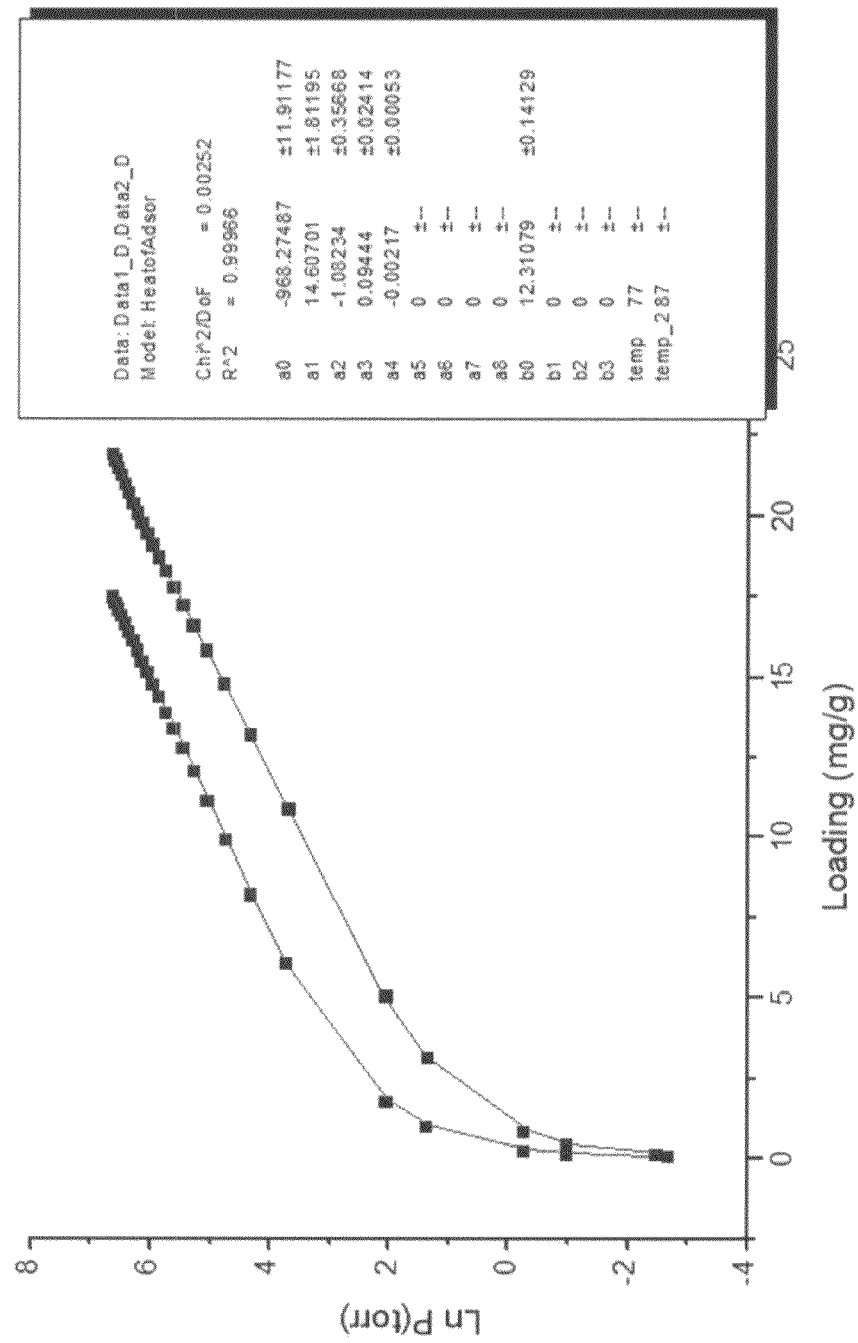
FIG. 25 depicts $H_2$ isotherms at 77K and 87K (black squares) and virial equation fits (red line) for 4 (II).
Figure 26:
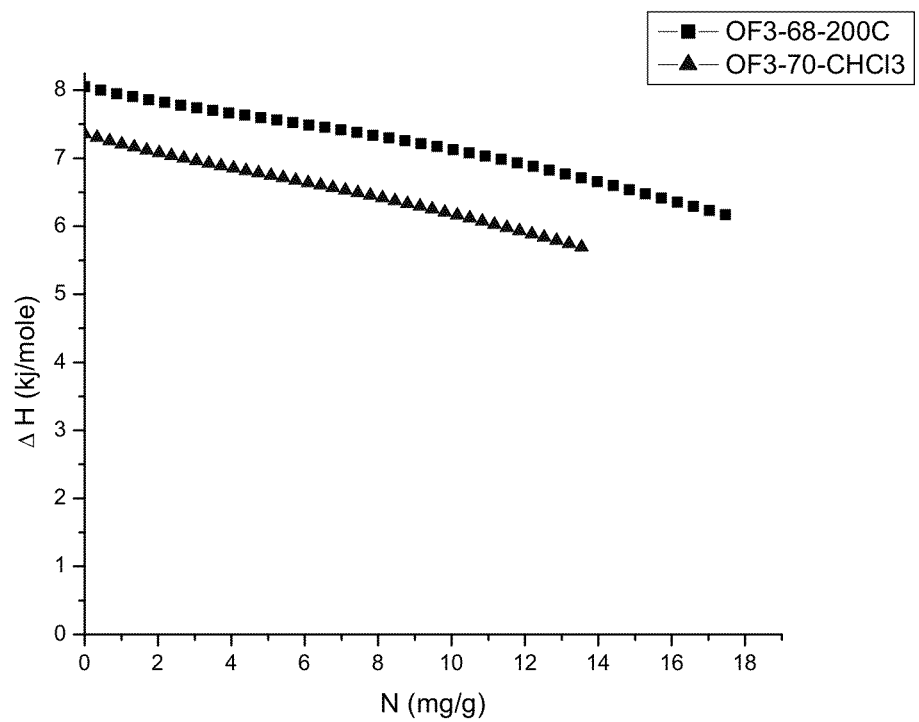
FIG. 26 depicts heats of adsorption ($\Delta H_{ads}$) for $H_2$ in 3'(blue) and 4 (black).

$CO_2$ adsorption (T=273 K) was used to determine the accessible surface areas and pore volumes of the original and cavity-modified MOFs (See Table 2 and FIG. 22). The areas range from 310 to 1370 $m^2/g$; the volumes range from 0.106 to 0.404 $cm^3/g$, with the volume for the "empty cavity" MOF (4) being the largest. With these results in hand, the sorption measurements were extended to molecular hydrogen. At 77 K and 1 atm, 4 displays reasonably high $H_2$ uptake: [18] 2.2% at 1 atm—roughly double the uptake by 3'. The difference can be attributed to the greater surface area for 4, as well as greater heats of adsorption (presumably due to open metal sites).

Figure 10:
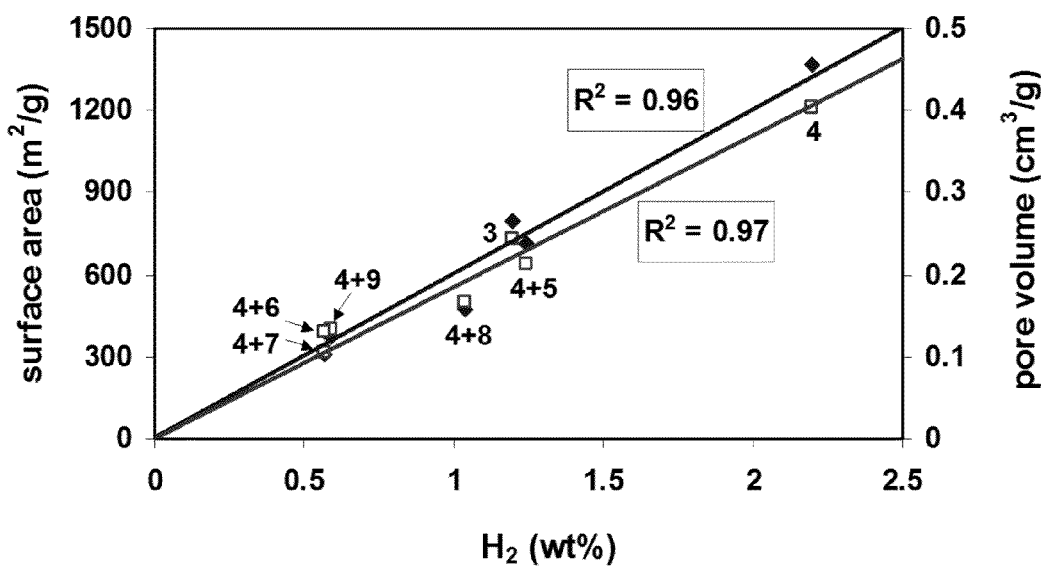
FIG. 10 depicts $H_2$ uptake versus pore volume (red, open squares) and surface area (blue, diamonds).
Figure 11:
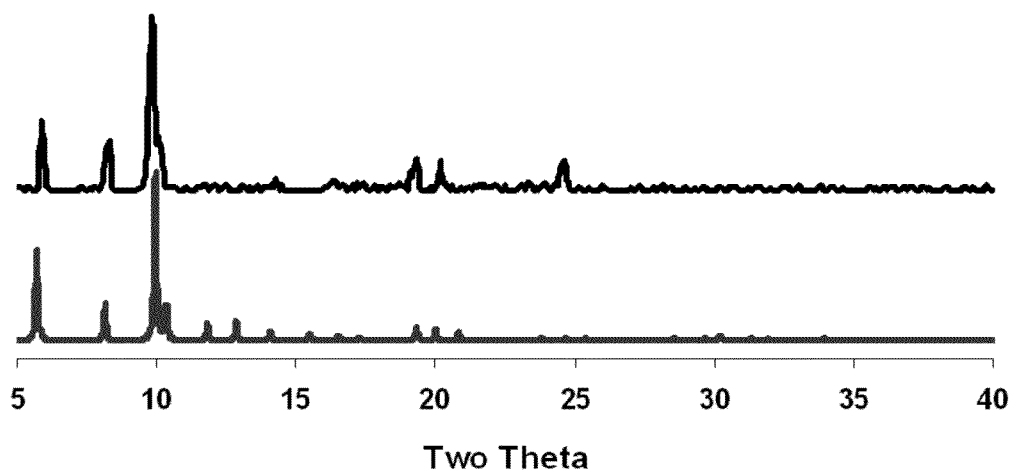
FIG. 11 depicts the simulated (bottom) and "as synthesized" bulk (top) powder x-ray diffraction patterns for 3.
Figure 12:
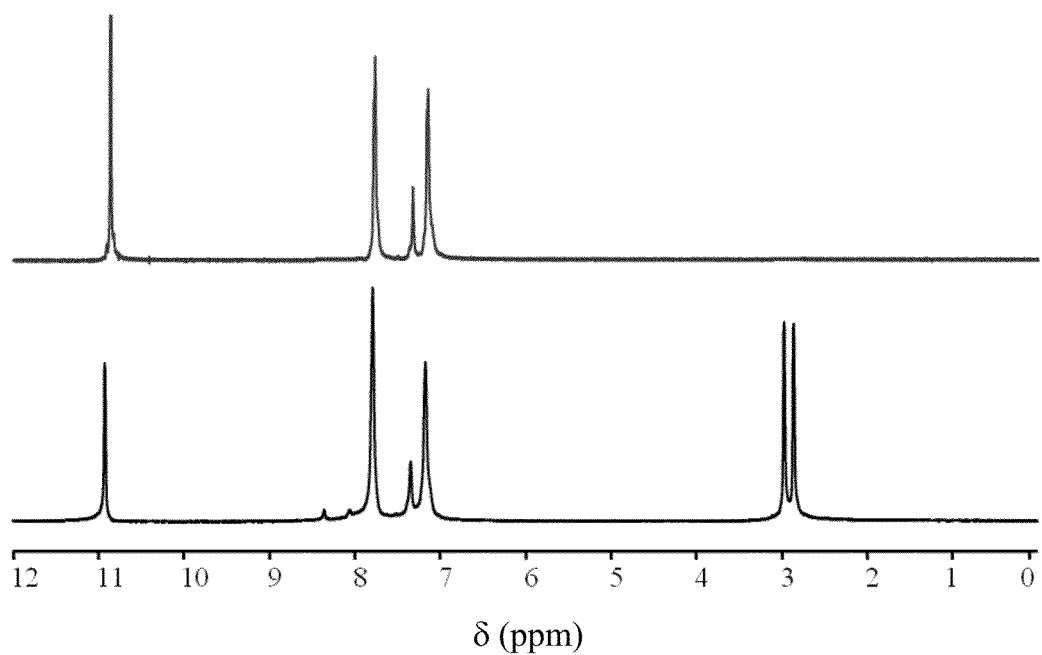
FIG. 12 shows the $^1$NMR spectra in $D_2SO_4/D_2O$ of 3' (bottom) and 4 (top).
Figure 13:
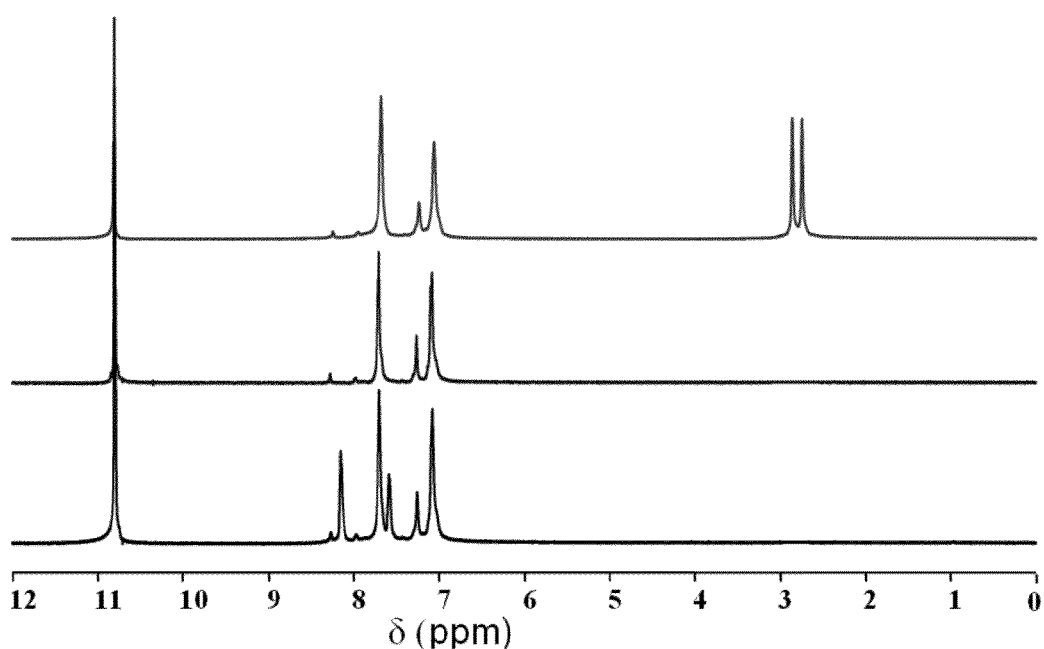
FIG. 13 shows the $^1$NMR spectra in $D_2SO_4/D_2O$ of 3' (top), 4 (middle) and 4+5 (bottom).
Figure 14:
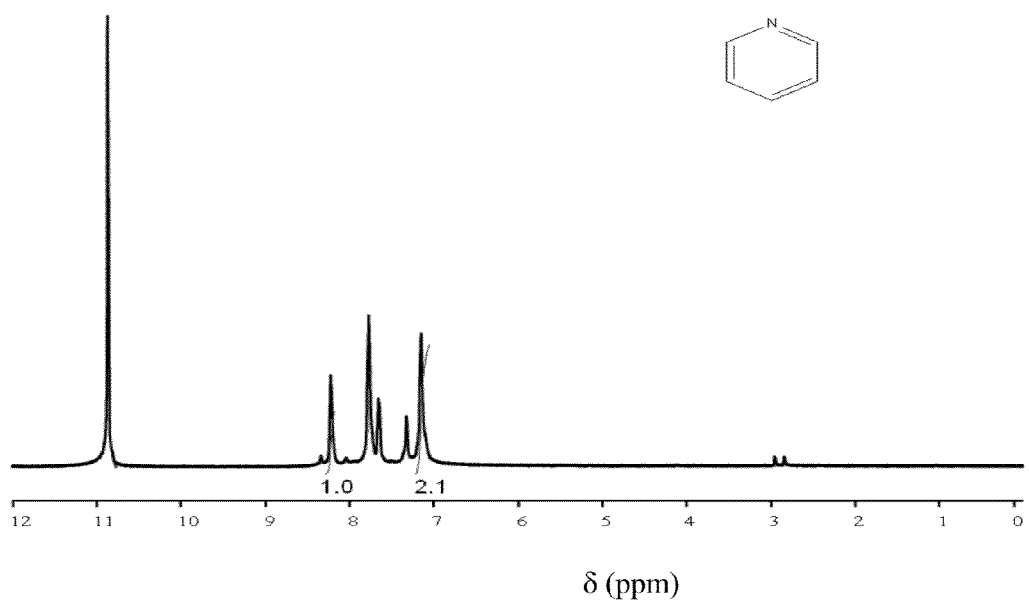
FIG. 14 shows the $^1$NMR spectra in $D_2SO_4/D_2O$ of 4+5.
Figure 15:
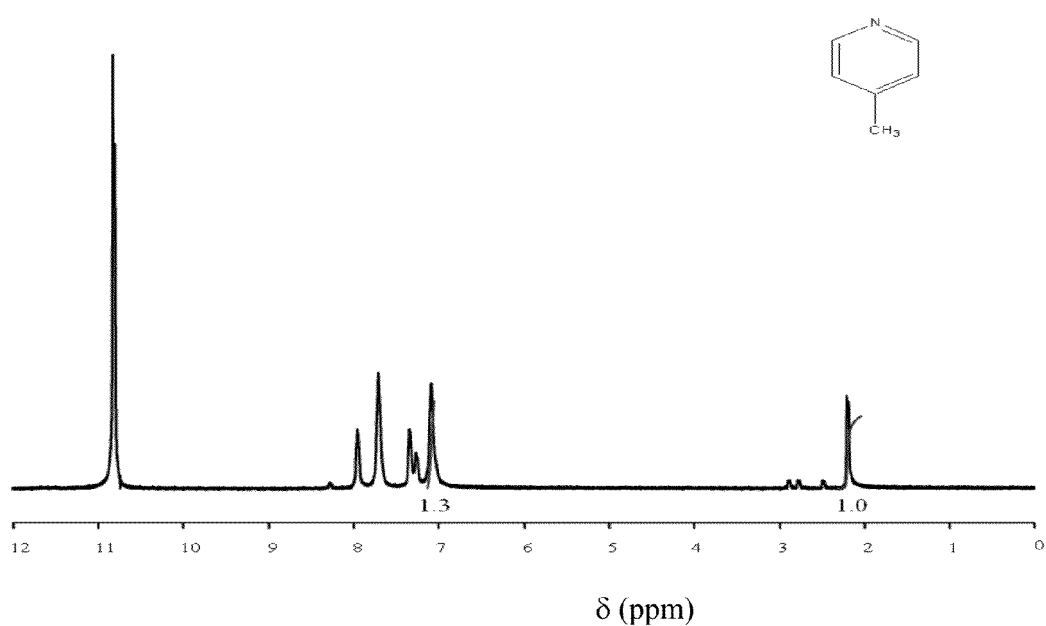
FIG. 15 shows the $^1$NMR spectra in $D_2SO_4/D_2O$ of 4+6.
Figure 16:
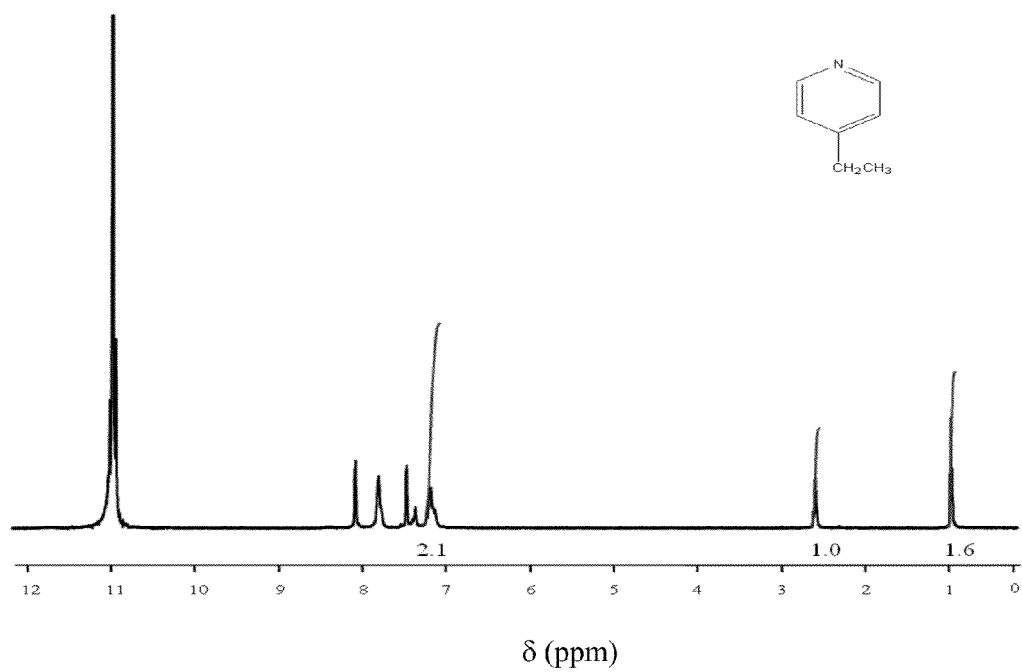
FIG. 16 shows the $^1$NMR spectra in $D_2SO_4/D_2O$ of 4+7.
Figure 17:
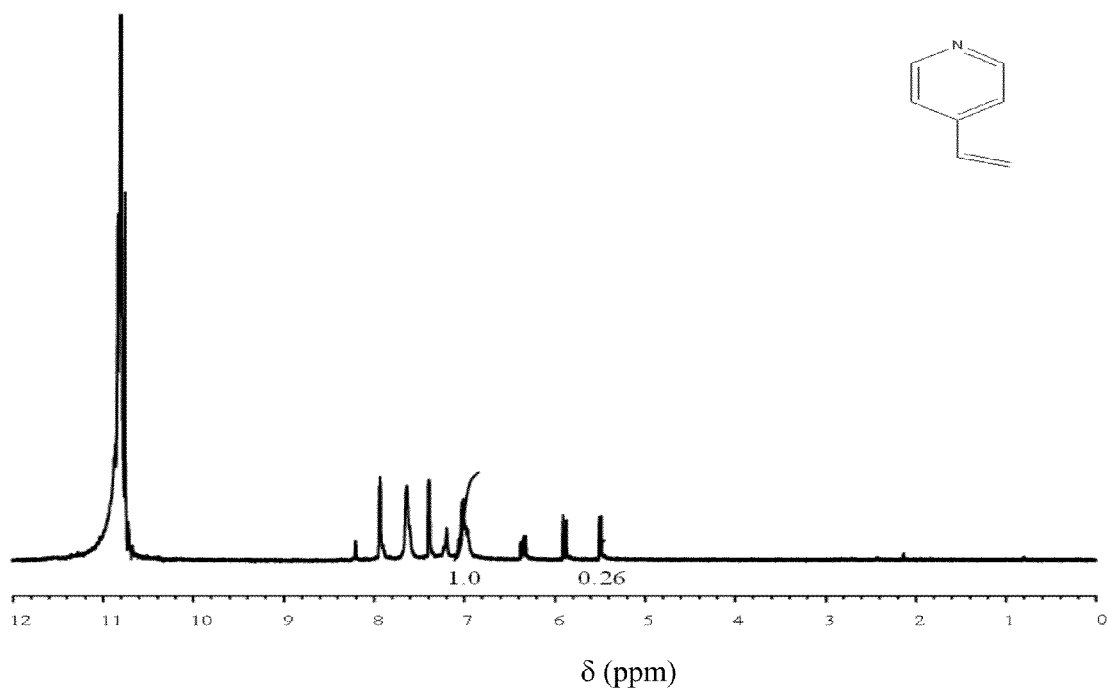
FIG. 17 shows the $^1$NMR spectra in $D_2SO_4/D_2O$ of 4+8.
Figure 18:
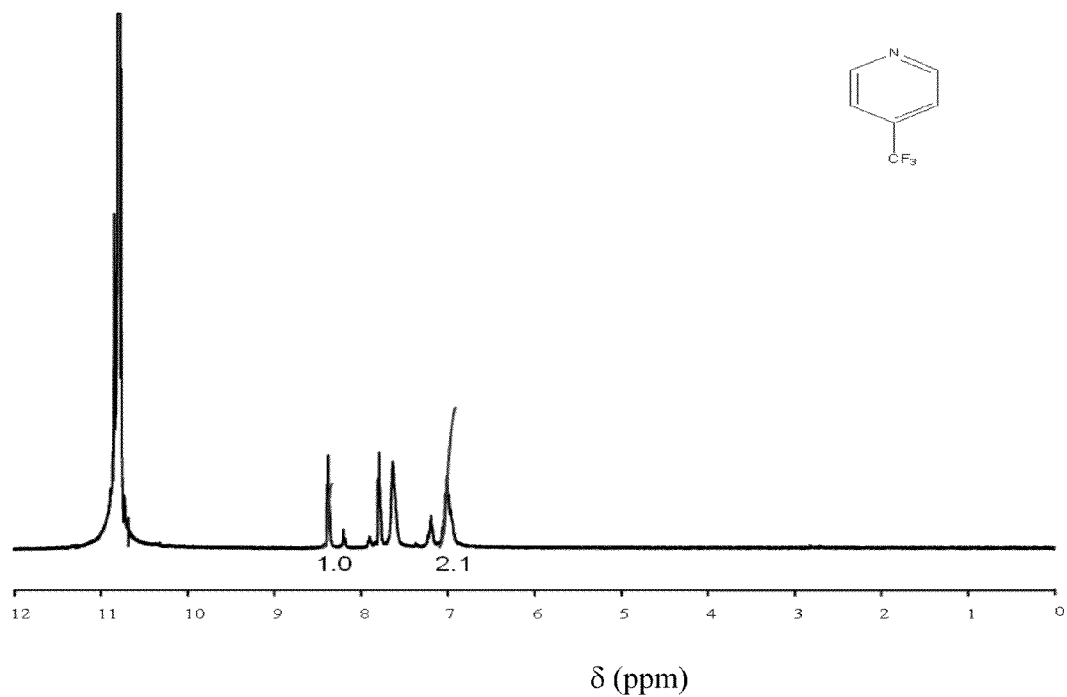
FIG. 18 shows the $^1$NMR spectra in $D_2SO_4/D_2O$ of 4+9.
Figure 19:
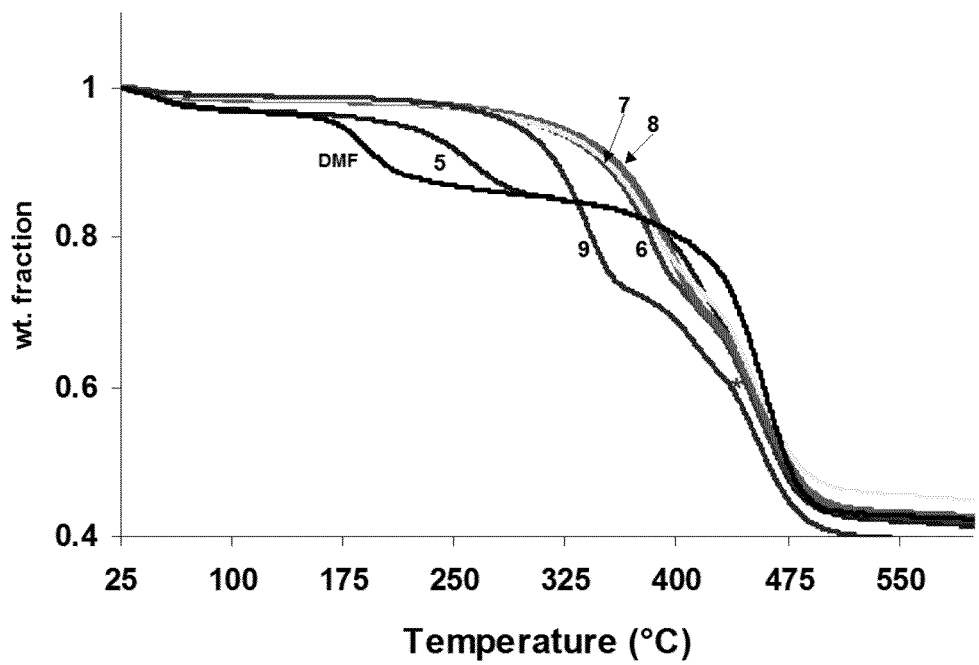
FIG. 19 depicts thermogravimetric analyses plots for the MOFs of the invention.
Figure 20:
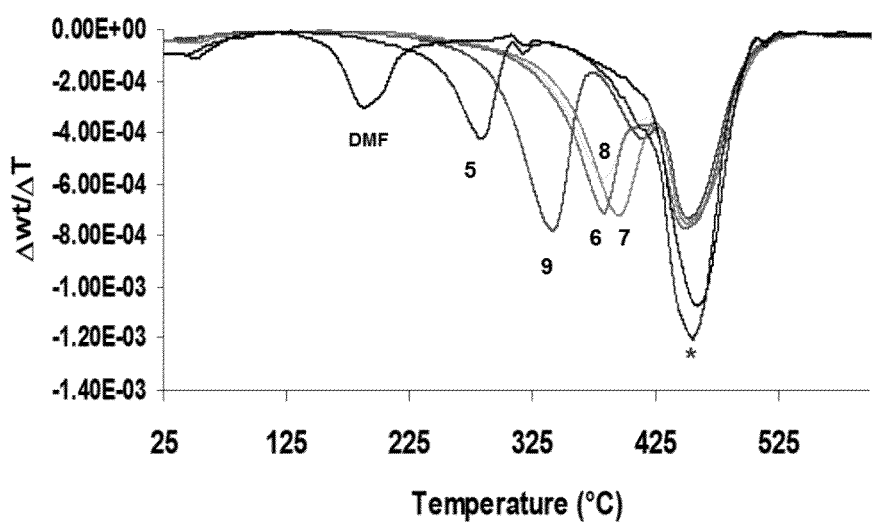
FIG. 20 depicts first-derivative thermogravimetric analyses plots for the MOFs of the invention.
Figure 21:
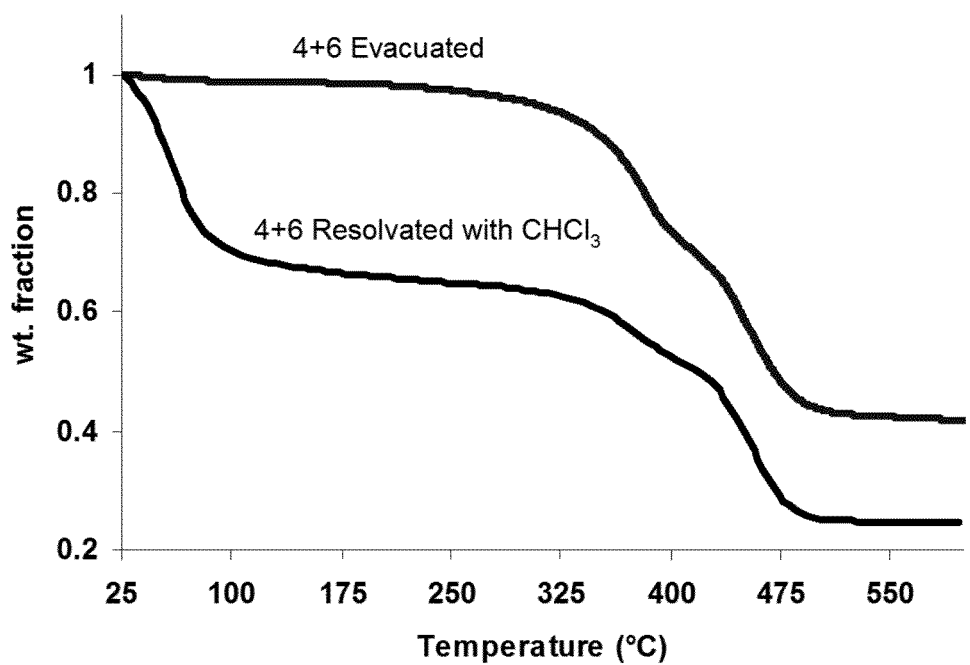
FIG. 21 depicts first-derivative thermogravimetric analyses plots for 4+6 evacuated at 150° C. (top) then resolvated with $CHCl_3$ (bottom).

FIG. 10 summarizes hydrogen uptake data for the "empty cavity" MOF and the six cavity-tailored variants. At 77 K and 1 atm. the range of gravimetric loadings for these otherwise identical compounds spans a rather remarkable factor of four. Consistent with expectations from recent computational studies,[19] the variations correlate well with both surface area and pore volume. While illustrating a relatively simple case (cryogenic $H_2$ uptake), the correlations clearly point to the potential for node-based, post-assembly modification for systematically altering sorption properties.

In another embodiment, cavity modification of 4 substantially altered the selectivity of the MOF for $CO_2$ versus methane. The adsorption in MOFs 3', 4, and 4+9 were compared. Single-component adsorption isotherms for $CO_2$, $N_2$, and $CH_4$ were measured experimentally in all three MOFs. Then, from the pure-component isotherms, the selectivities for $CO_2/N_2$ and $CO_2/CH_4$ mixtures were calculated using ideal adsorbed solution theory (IAST)[20].

Figure 27:
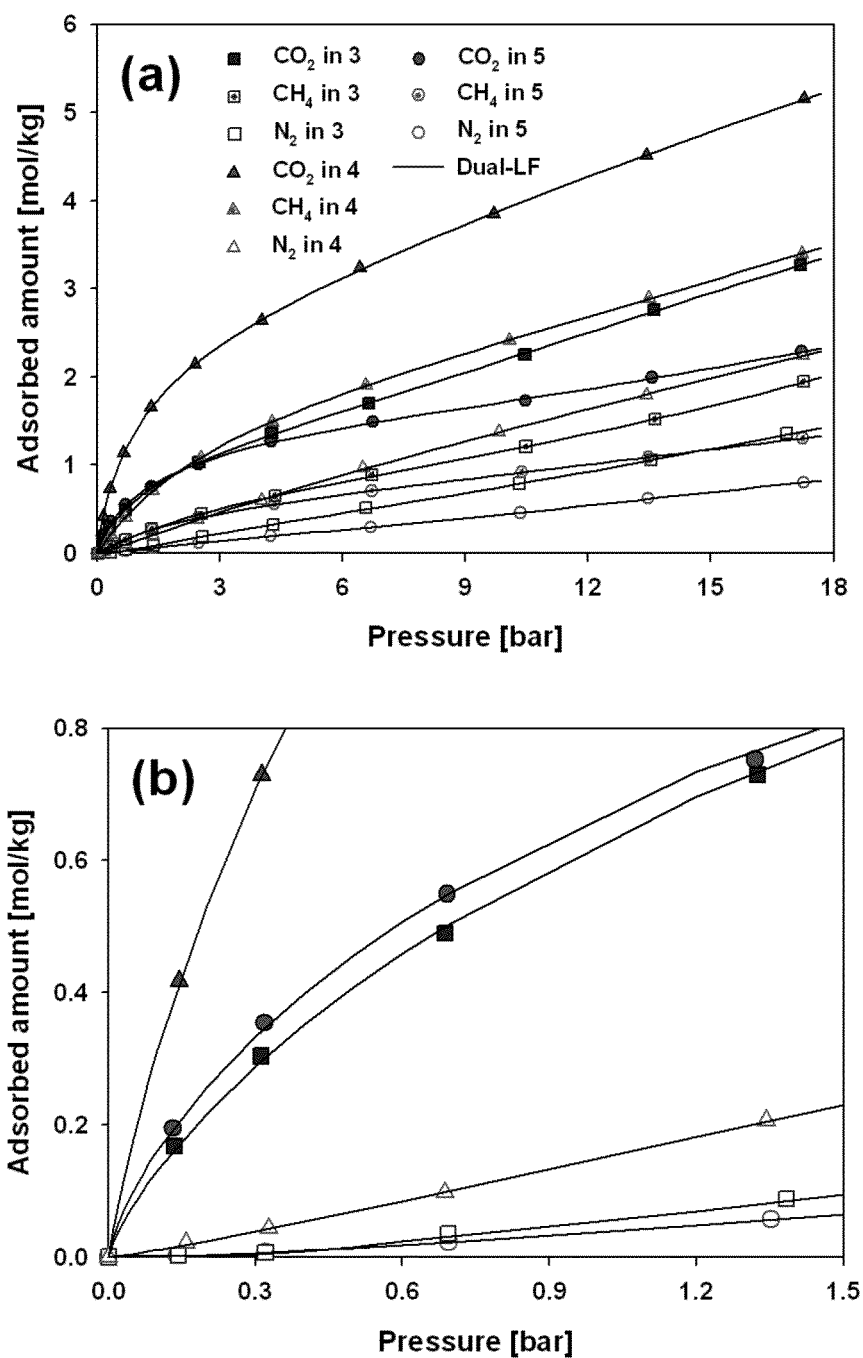
FIG. 27 depicts adsorption isotherms of $CO_2$, $N_2$, and $CH_4$ in 3', 4, and 4+9 at 298° K: (a) full pressure range, (b) low pressure range ($CH_4$ isotherms are omitted for clarity).

FIG. 27 shows the adsorption isotherms of $CO_2$, $N_2$, and $CH_4$ at 298 K up to 18 bar, measured volumetrically on evacuated samples of 3, 4, and 5. In each sample, $CO_2$ is the most strongly adsorbed molecule due to its large quadrupolar moment. Also, $CH_4$ shows stronger adsorption than $N_2$ as already reported in all known sorbents. This is attributed to the higher polarizability of $CH_4$ ($26 \times 10^{-25}$ $cm^{-3}$) VS. $N_2$ ($17.6 \times 10^{-25}$ $cm^{-3}$). Measurement of $N_2$ isotherms for any of the three MOFs at 77 K could not be made, but the materials did take up $N_2$ at 298 K. This suggested that the pores of 3', 4, and 4+9 may be close to the kinetic diameter of $N_2$ (3.64 Å). For such tightly constricted pores, a likely explanation was that $N_2$ molecules cannot enter the pores at 77 K due to large diffusional resistances, but at 298 K the additional thermal energy allows the molecules to overcome these resistances.

Figure 1:
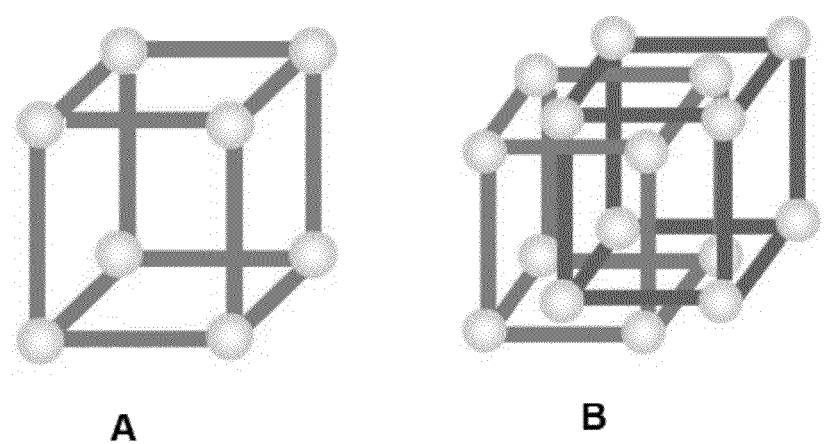
FIG. 1 is a diagram of a A) noncatenated structure and a B) catenated structure.
Figure 2A:
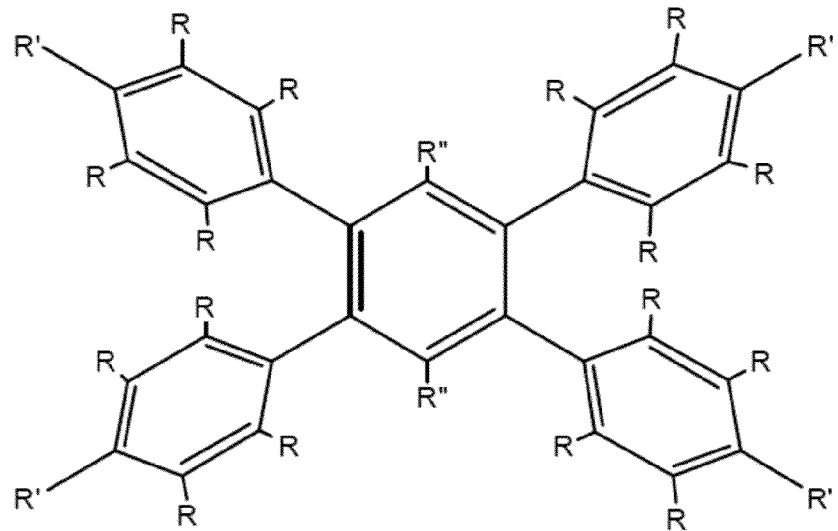
FIGS. 2A-C represent ligands of the sort useful in accordance with this invention.
Figure 2B:
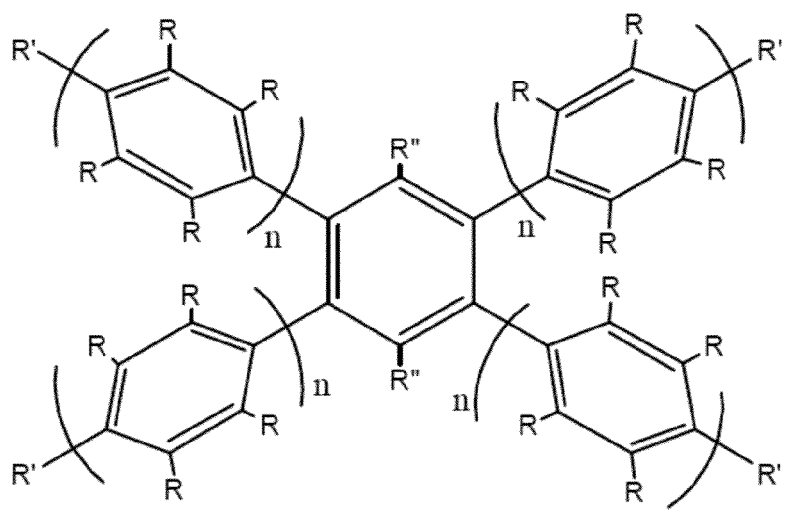
Figure 2C:
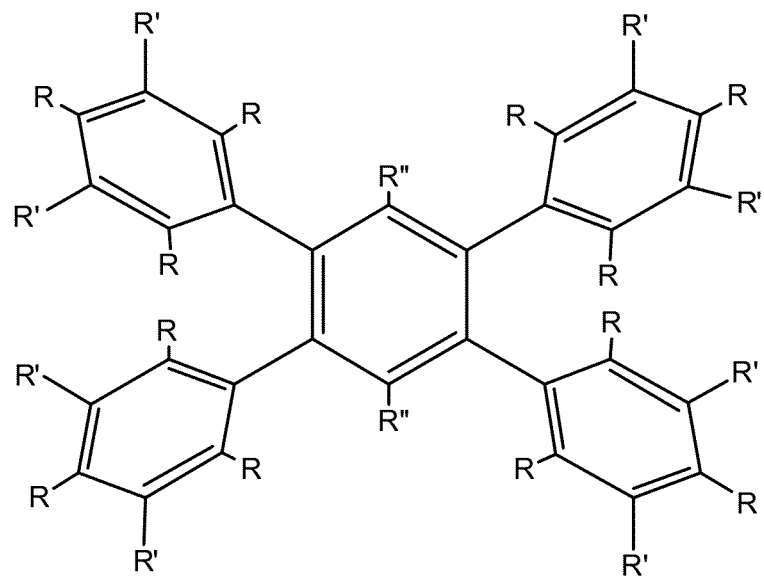
Figure 3:
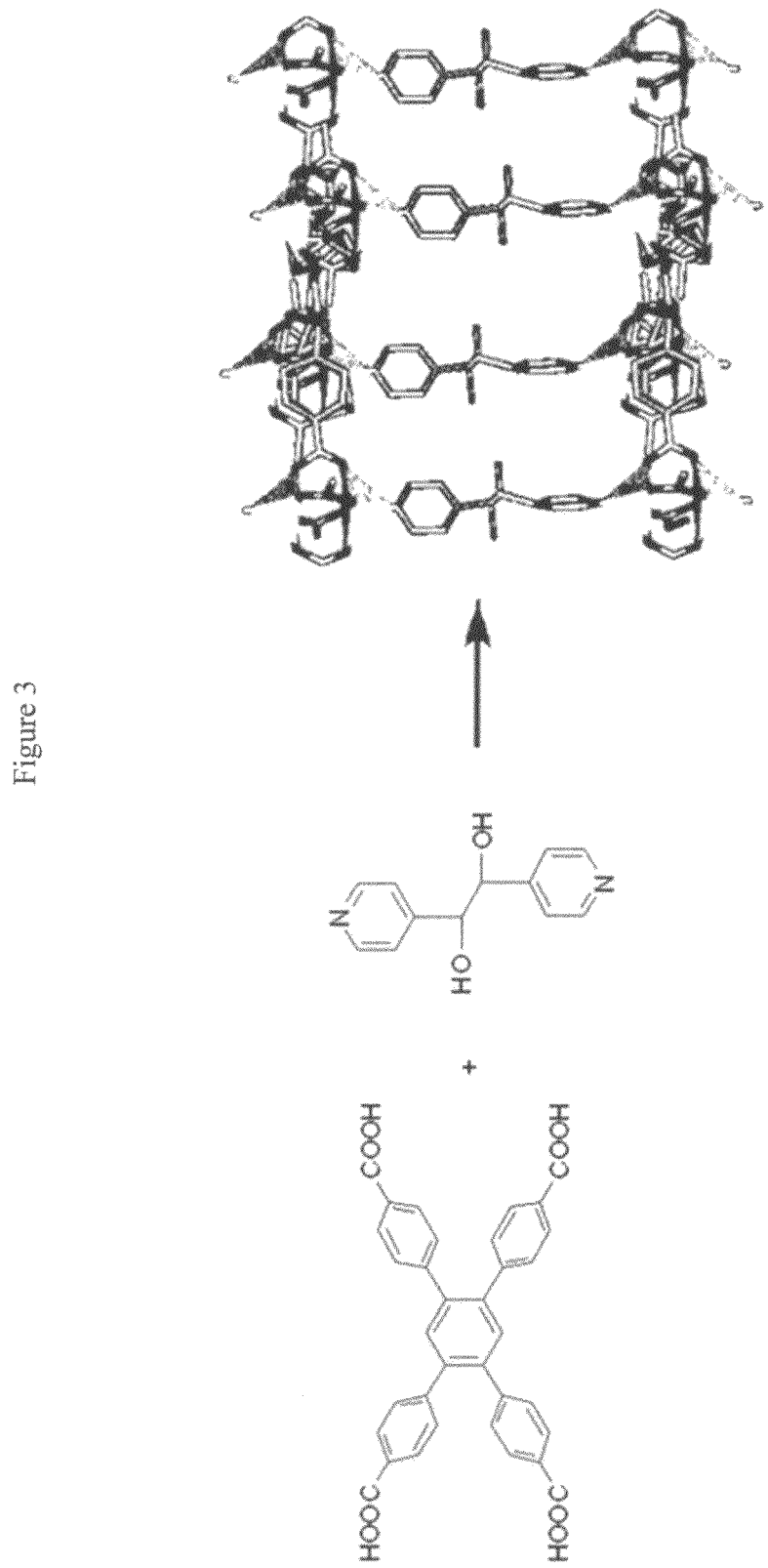
FIG. 3 is an example of a noncatenated MOF with a large cavity that can be used for hydrogen, carbon dioxide and methane storage and/or separation.
Figure 4:
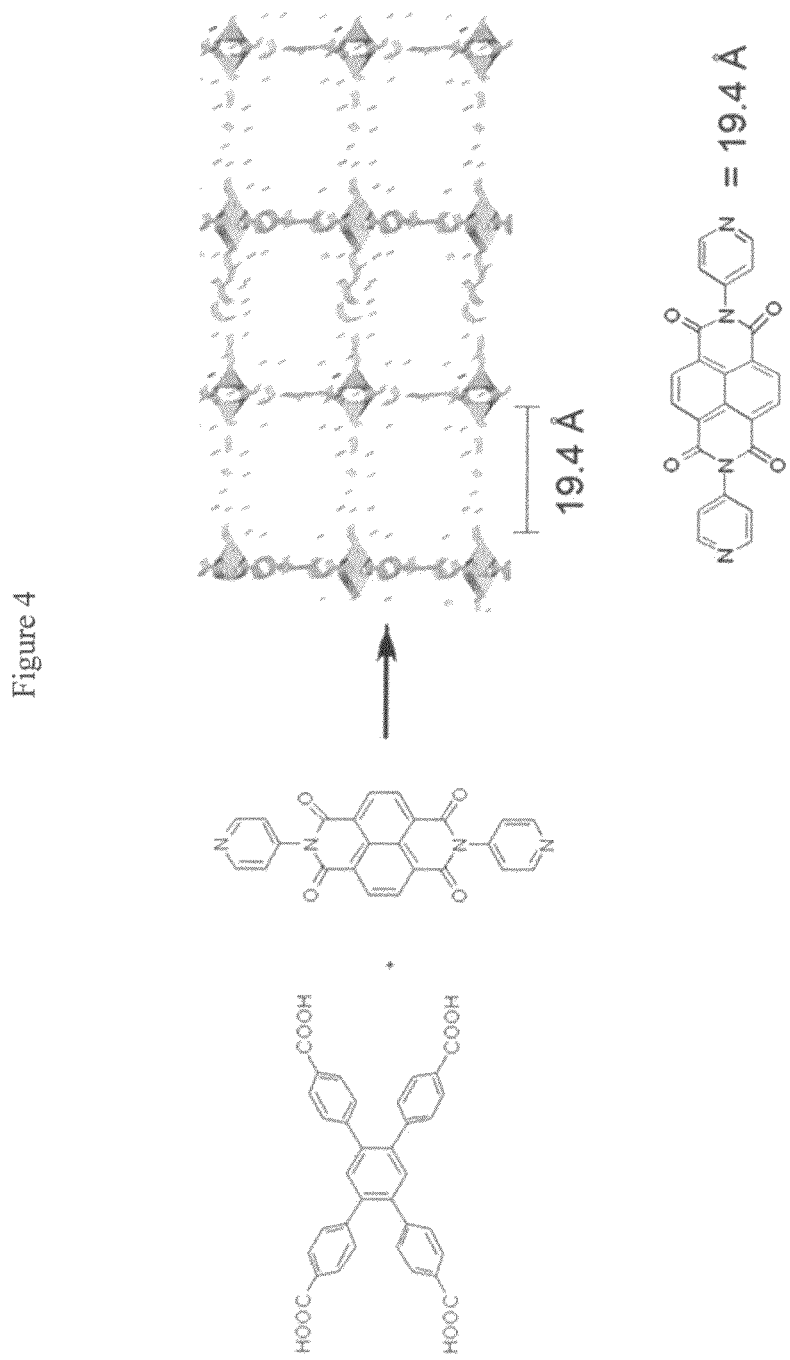
FIG. 4 is another example of a noncatenated MOF with a large cavity that can be used for hydrogen, carbon dioxide and methane storage and/or separation.
Figure 5:
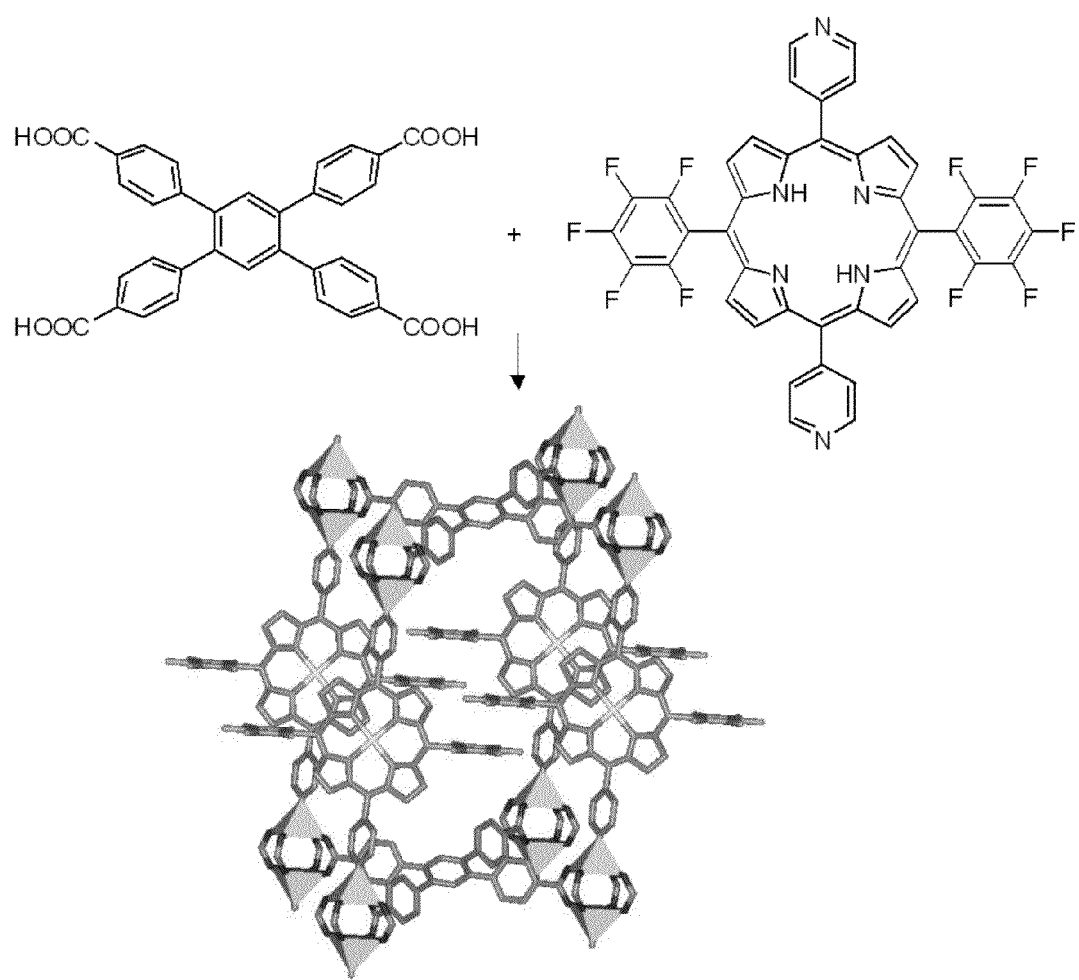
FIG. 5 is an example of a noncatenated MOF with a large cavity that can be used for catalysis.

None of the isotherms in FIG. 27 showed saturation at 18 bar. For all gases, the order of the adsorbed amounts around 18 bar was as follows: 4>3'>4+9 (FIG. 2A). At low pressures, 4 again showed the highest adsorption of the three MOFs for all three gases (FIG. 2b), presumably due to strong adsorption on the open-metal sites rather than the larger surface area of 4. At low loading, the py-$CF_3$-modified MOF 4+9 adsorbs more $CO_2$ than 3 at 298 K, but less $N_2$ and $CH_4$.

Figure 28:
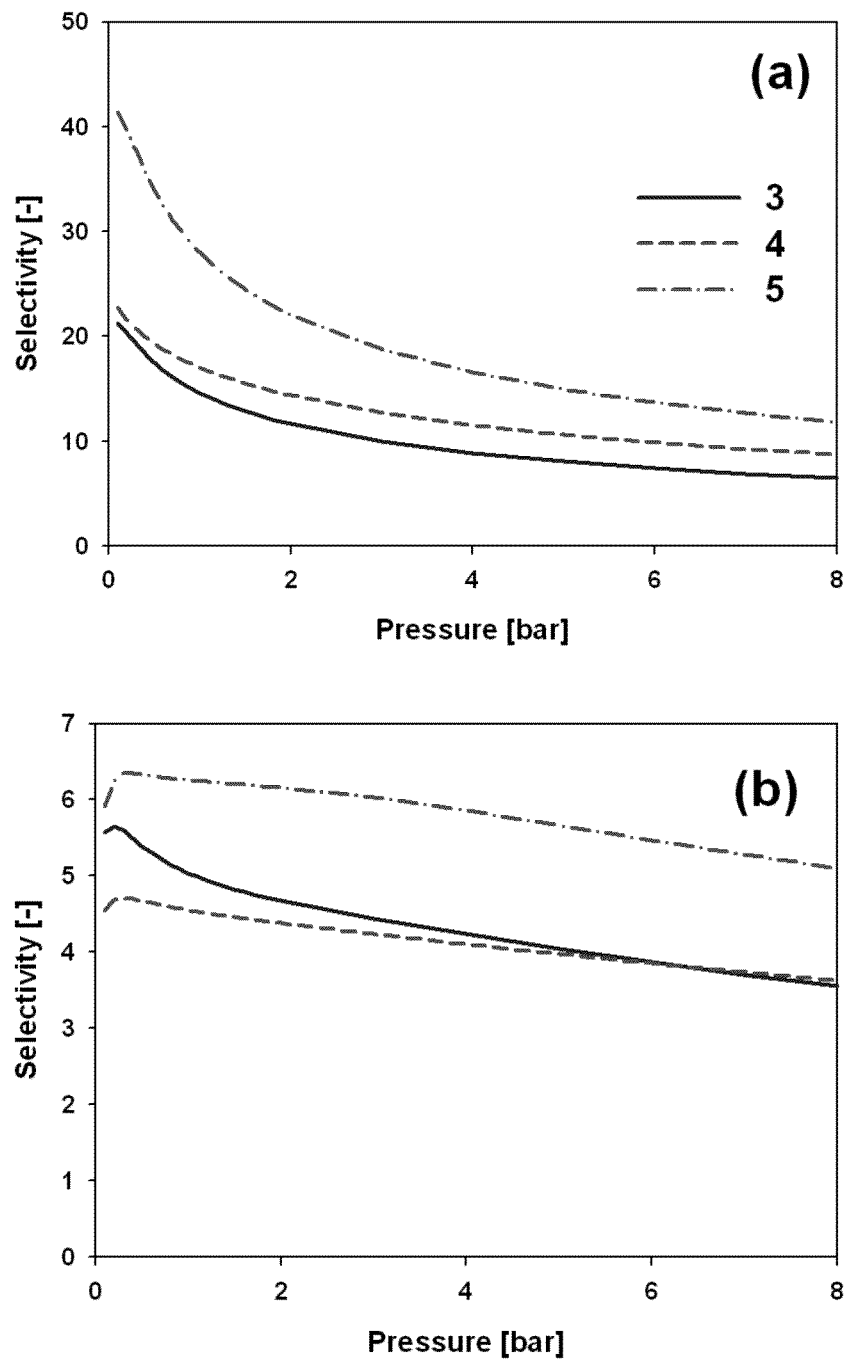
FIG. 28 shows ideal adsorption solution theory selectivities of (a) $CO_2$ over $N_2$, and (b) $CO_2$ over $CH_4$ for equimolar binary mixtures in 3', 4, and 4+9 at 298° K.

The selectivities of $CO_2/N_2$ and $CO_2/CH_4$ binary mixtures were predicted from the experimental single-component isotherms using IAST. FIGS. 28a and 28b present the predicted selectivities for equimolar $CO_2/N_2$ and $CO_2/CH_4$ mixtures in 3', 4, and 4+9 as a function of total bulk pressure. The most remarkable point of FIG. 28 was the high $CO_2/N_2$ selectivity (~42) of 4+9 at low pressure. Throughout the entire pressure range, 4+9 exhibited larger $CO_2/N_2$ and $CO_2/CH_4$ selectivities than 3' and 4. The following explanations were surmised: a) first, the highly polar —$CF_3$ groups in 5 should be more attractive to $CO_2$ (large quadrupole moment, 13.4 C $m^2$) than $N_2$ (smaller quadrupole moment, 4.7 C $m^2$) or $CH_4$ (nonpolar); and b) second, the more constricted pores of 4+9 should enhance the selectivity of the more strongly adsorbed $CO_2$ over $N_2$ and $CH_4$ due to the increased potential.

Figure 29:
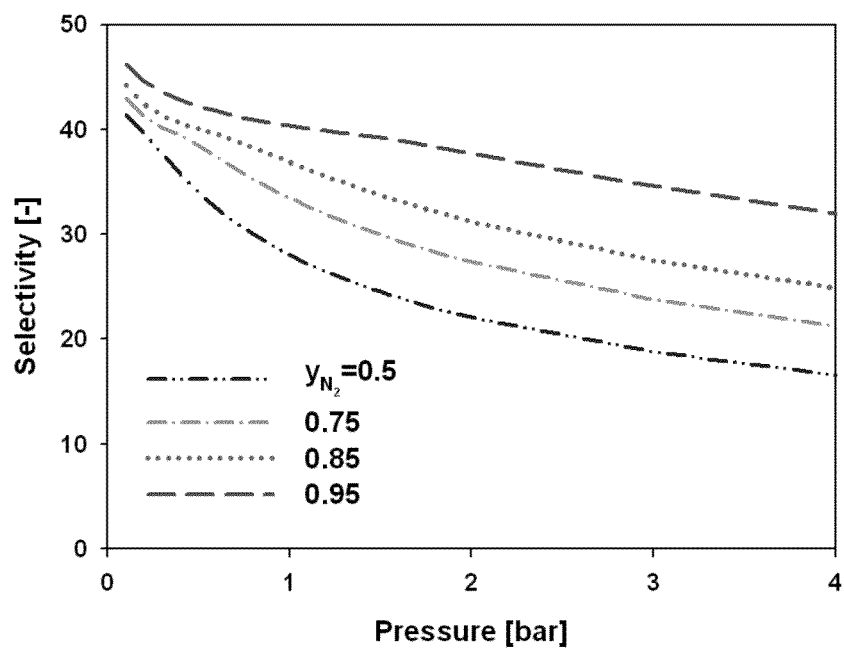
FIG. 29 shows ideal adsorption solution theory selectivities of $CO_2$ over $N_2$ in 9 at different pressures and mixture compositions.

FIG. 29 shows the $CO_2/N_2$ selectivities in 4+9 at different pressures and different mixture compositions predicted by IAST. The selectivity increased with decreasing pressure. Also, the selectivity increased as $y_{N2}$ approached unity, but at zero coverage it did not depend on the gas composition. For the case of $y_{N2}=0.85$, which is a typical composition for flue gas from power plants, the selectivity was in the range of 25-45. In addition, the selectivity was high (30-37), at or slightly above atmospheric pressure, the pressure regime of interest for removing $CO_2$ from flue gas. For these conditions, the selectivity of 4+9 was higher than that of Cu-BTC (20-22 as predicted by molecular simulation), the largest previously reported for MOFs.[21] Moreover, these selectivities were considerably higher than the experimental $CO_2/N_2$ selectivities reported for zeolite and carbon adsorbents under similar conditions: zeolite 4A (19), zeolite 13X (18), activated carbon (15).

Figure 30:
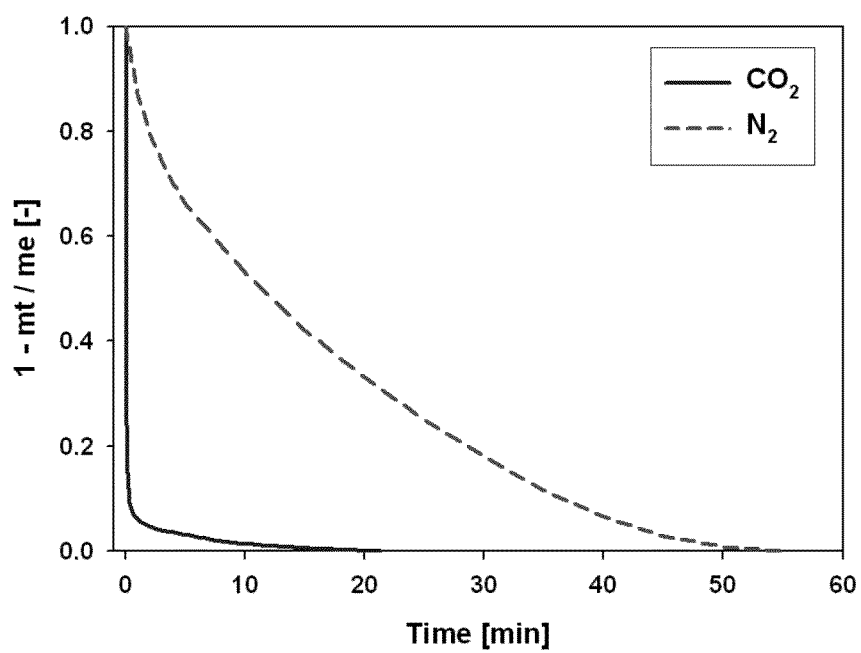
FIG. 30 depicts adsorption rates of $CO_2$ and $N_2$ in 4+9 at 298° K (at the $1^{st}$ adsorption points). mt is the amount adsorbed at time t, and me is the equilibrium amount adsorbed.
Figure 31:
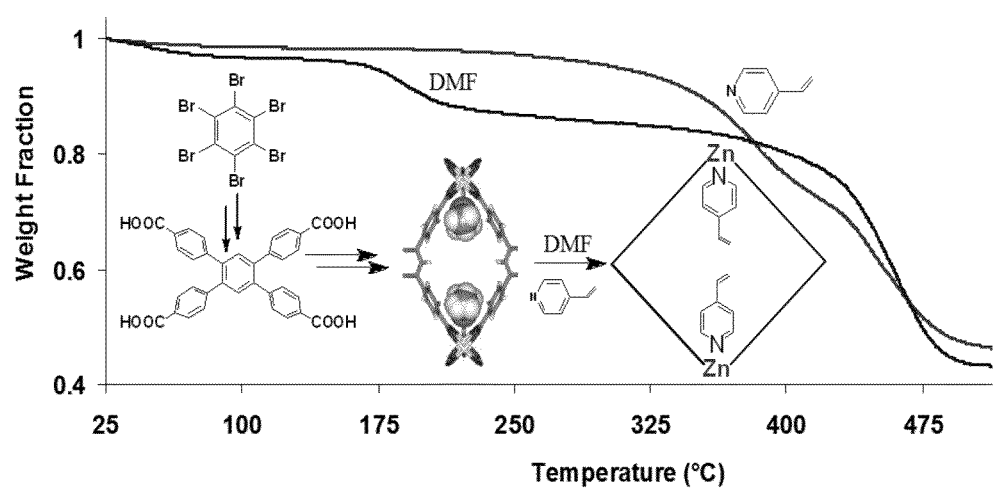
FIG. 31 depicts thermogravimetric analyses plots for 3 and 4 of the invention.

For PSA processes, the kinetics and reversibility of adsorption were also important. Adsorption of $CO_2$ was found to be completely reversible in 4+9 (FIG. 22), and a graph of the time evolution for $CO_2$ and $N_2$ adsorption in 4+9 at the first point of the isotherms (0.25 atm and 298 K) showed that the adsorption rate of $CO_2$ is much faster than that of $N_2$ (FIG. 30). Thus, selectivity of $CO_2$ over $N_2$ would increase even more if the adsorption kinetics were considered in addition to the adsorption equilibria. The fast and reversible adsorption of $CO_2$ in 4+9, along with the high selectivity, indicated that this material is an attractive candidate for the adsorptive separation of $CO_2$ from $N_2$.

EXAMPLES OF THE INVENTION

General information. Starting materials were purchased from Sigma-Aldrich (ACS grade) and used without further purification unless otherwise noted.

Thermogravimetric analyses (TGA) were performed on a Mettler-Toledo TGA/SDTA851e. Powder X-ray diffraction (PXRD) patterns were recorded with a Rigaku XDS 2000 diffractometer using nickel-filtered Cu Kα radiation (λ=1.5418 Å). Adsorption isotherms were measured with an Autosorb 1-MP from Quantachrome Instruments. $^1H$ NMR and $^{13}C$ NMR were done on a Varian Inova 500 spectrometer at 500 MHz and 125 MHz respectively. Single crystals were mounted on a Bruker SMART CCD 1000 diffractometer equipped with a graphite-monochromated MoKa (λ=0.71073 Å) radiation source in a cold nitrogen stream.

Example 1

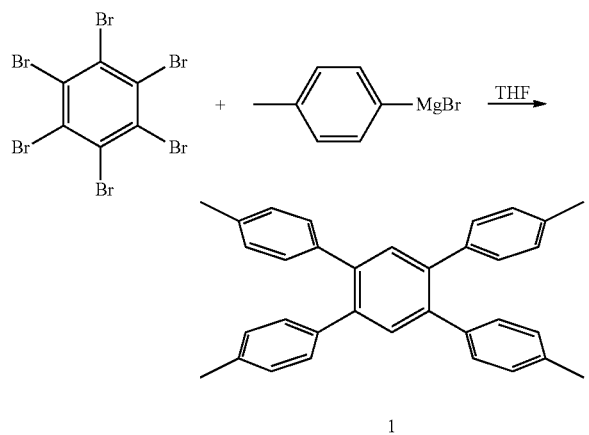

1

Synthesis of 1: 200 ml of (1M in THF, 200 mmol) p-tolylmagnesium bromide was added under nitrogen to a flask containing 5 g of benzene hexabromide (9.07 mmol). The mixture was stirred at room temperature for 15 hours (gray suspension). The reaction was quenched with ice followed by 6M HCl. The mixture was extracted with hexanes (3×250 ml). The organics were combined and the solvent was removed via rotary evaporation. The solid was then washed with hexanes and collected by filtration. Isolated yield: 2.8 g, 70%. $^1$H NMR (CDCl$_3$): δ2.32 (s, 12H), 7.04 (d, 8H), 7.12 (d, 8H), 7.45 (s, 2H). $^{13}$C NMR (CDCl$_3$): δ21.4, 128.9, 130.0, 133.3, 136.4, 138.4, 139.5.

Example 2

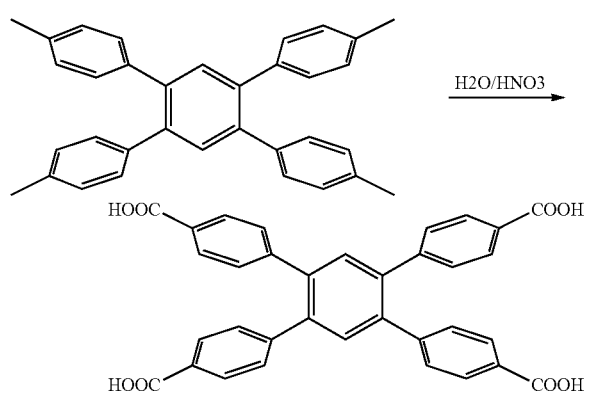

2

Synthesis of 2: 4 g of 1 was placed in a teflon lined vessel. 45 ml of water and 15 ml of HNO$_3$ were then added. The vessel was sealed and heated at 180° C. for 24 hrs. The resulting solid was collected by filtration and washed with THF/CHCl$_3$. Isolated yield: 3.8 g, 75%. $^1$H NMR (CDCl$_3$): δ7.40 (d, 8H), 7.60 (s, 2H), 7.80 (d, 8H), 10.00 (s, 4H). $^{13}$C NMR (CDCl$_3$): δ129.9, 130.7, 133.1, 135.4, 139.9, 146.3, 192.0.

Example 3

Synthesis of 3: X-ray quality single crystals of 6 were obtained upon heating Zn(NO$_3$)$_2$.6H$_2$O (20 mg, 0.067 mmol), 2(10 mg, 0.018 mmol) in 1 ml of DMF at 80° C. for 24 hours. Isolated yield: 50% yield based on 2. This procedure can be scaled up using the same solution concentrations.

Example 4

Single crystal X-ray diffraction: Single crystals of 3 were mounted on a BRUKER APEX2 V2.1-0 diffractometer equipped with a graphite-monochromated MoKa (λ=0.71073 Å) radiation source in a cold nitrogen stream. All crystallographic data were corrected for Lorentz and polarization effects (SAINT). The structures were solved by direct methods and refined by the full-matrix least-squares method on F$^2$ with appropriate software implemented in the SHELXTL program package. All non-hydrogen atoms were refined anisotropically. Hydrogen atoms were added at their geometrically ideal positions. Most of the solvent molecules occupying the pores were severely disordered, which hindered satisfactory development of the model; therefore, the SQUEEZE routine (PLATON) was applied to remove the contributions of electron density from disordered solvent molecules. The outputs from the SQUEEZE calculations are shown in Table 1.

TABLE 1

Crystal data and structure refinement for 3

| | 3 |
|---|---|
| empirical formula | C$_{20}$H$_{16}$NO$_5$Zn |
| formula weight | 415.71 |
| crystal color, habit | colorless, tabular |
| crystal dimension (mm$^3$) | 0.151 × 0.105 × 0.032 |
| crystal system | orthorhombic |
| space group | Imma |
| a (Å) | 21.6546(16) |
| b (Å) | 30.901(2) |
| c (Å) | 9.2945(8) |
| α (deg) | 90 |
| β (deg) | 90 |
| γ (deg) | 90 |
| V (Å$^3$) | 6219.3(8) |
| Z | 8 |
| ρ (calcd, g/cm$^3$) | 0.888 |
| μ (cm$^{-1}$) | 0.808 |
| goodness-of-fit on F$^2$ | 0.838 |
| R | 0.1009 |
| R$_w$ | 0.2530 |

Example 5

Synthesis of 3': crystals of 3 were evacuated while heating at 100° C. for 24 hours.

Example 6

Synthesis of 4: crystals of 3 were evacuated while heating at 100° C. for 12 hours then 150° C. for 12 hours.

Example 7

Synthesis of Modified 4: 50 mg of 4 was soaked for 24 hours in a solution of 3 ml of $CHCl_3$ and 1 ml of the pyridine derivative. The solid was filtered and evacuated while heating at 150° C. for 12 hours.

Example 8

$^1$H NMR of Modified MOF: 5 mg of the modified MOF was dissolved in $D_2SO_4/D_2O$. NMR spectra were obtained after the solid completely dissolved (See FIGS. 8 and 12-18).

Example 9

Adsorption measurements: Samples of known weight evacuated at the appropriate temperature under $10^{-5}$ torr dynamic vacuum for 24 hours on an Autosorb 1-MP from Quantachrome Instruments prior to gas adsorption measurements. The evacuated sample was weighed again to obtain the sample weight.

TABLE 2

$H_2$ uptake, surface areas, and pore volumes

| MOF | $H_2$-uptake (wt %) | Surface Area ($m^2/g$) | Pore Volume ($cm^3/g$) |
|---|---|---|---|
| 3' | 1.20 | 796 | 0.244 |
| 4 | 2.20 | 1366 | 0.404 |
| 4 + 5 | 1.24 | 709 | 0.214 |
| 4 + 6 | 0.59 | 370 | 0.132 |
| 4 + 7 | 0.57 | 309 | 0.106 |
| 4 + 8 | 1.04 | 473 | 0.165 |
| 4 + 9 | 0.57 | 388 | 0.131 |

Example 10

Isosteric heat of adsorption: The hydrogen isotherms obtained at 77 and 87 K were fit to the following virial equation: (Czepirski, L.; Jagiello, J., *Chem. Eng. Sci.* 1989, 44, 797.

$$\ln p = \ln N + \frac{1}{T}\sum_{i=0}^{m} a_i N^i + \sum_{i=0}^{n} b_i N^i$$

The heats of adsorption of 3 and 4 were calculated from the fitting parameters in the following equation:

$$q_{st}(N) = -R\sum_{i=0}^{m} a_i N^i$$

As demonstrated, a robust, non-catenated, and permanently microporous metal-organic framework (MOF) material has been synthesized by combining a new representative nonplanar ligand, 4,4',4",4'''-benzene-1,2,4,5-tetrayl-tetrabenzoic acid, with a Zn(II) source under solvothermal conditions. The new material features cavities that are readily modified via activation and functionalization of framework nodes. Investigation of the "empty cavity" version of the material and six cavity-modified versions reveals that modification can substantially modulate the MOF's internal surface area and pore volume. The resulting tailored cavities show differing degrees of uptake of molecular hydrogen under cryogenic conditions—an observation that may foreshadow a range of other applications, including cavity tuning of chemical catalysis and chemical separations.

Specifically, experimental isotherms and IAST calculations have shown that the MOFs of the invention are a promising material for $CO_2/N_2$ separations. In addition, they provide preliminary insight into the factors of most importance for adsorption selectivity of $CO_2$, $N_2$, and $CH_4$ mixtures in MOFs. Post-synthesis modification of MOFs by replacing coordinated solvent molecules with highly polar ligands or ligands featuring other chemical functionalities may be a powerful method for generating new sorbents for other difficult separations.

Thus, without limitation, the present invention can be utilized in the context of gas storage, gas/small molecule separations, gas/small molecules sensing, chemical catalysis and chemical protection.

Various aspects and features of this invention can be considered in the context of the following references, as enumerated above.

1. Recent reviews: (a) Collins, D. J.; Zhou, H-C. *J. Mat. Chem.* 2007, 17, 3154-3160. (b) Férey, G. *Chem. Soc. Rev.*, 2008, 37, 191-214.
2. (a) Lee, E. Y.; Jang, S. Y.; Suh, M. P. *J. Am. Chem. Soc.* 2005, 127, 6374-6381. (b) Dinca, M.; Long, J. R. *J. Am. Chem. Soc.* 2005, 127, 9376-9377. (c) Snurr, R. Q.; Hupp, J. T.; Nguyen, S. T. *AIChE*, 2004, 50, 1090-1095. (d) Bae, Y. S.; Mulfort, K. L.; Frost, H.; Ryan, P.; Punnathanam, S.; Broadbelt, L. J.; Hupp, J. T.; Snurr, R. Q., *Langmuir*, 2008, ASAP, DOI: 10.1021/la800555x. (e) Bae, Y. S.; Farha, O. K.; Spokoyny, A. M.; Mirkin, C. A.; Hupp, J. T.; Snurr, R. Q., *Chem. Commun.*, 2008, 4135-4137.
3. (a) S.-H. Cho, B. Ma, S. T. Nguyen, J. T. Hupp, T. E. Albrecht-Schmitt, *Chem. Commun.* 2006, 2563-2565. (b) J. S. Seo, D. Wand, H. Lee, S. I. Jun, J. Oh, Y. Jeon, K. Kim *Nature* 2000, 404, 982-986. (c) T. Sawaki, Y. Aoyama, *J. Am. Chem. Soc.* 1999, 121, 4793-4798. (d) B. Kesanli, W. Lin, *Coord. Chem. Rev.* 2003, 246, 305-326. (e) A. Hu, H. L. Ngo, W. Lin, *J. Am. Chem. Soc.* 2003, 125, 11490-11491. (f) C.-D. Wu, A. Hu, L. Zhang, W. Lin, *J. Am. Chem. Soc.* 2005, 127, 8940-8941. (g) M. Fujita, Y.-J. Kwon, S. Washizu, K. Ogura, *J. Am. Chem. Soc.* 1994, 116, 1151-1152.
4. (a) Nouar, F.; Eubank, J. F.; Bousquet, T.; Wojtas, L.; Zaworotko, M. J.; Eddaoudi, M. *J. Am. Chem. Soc.* 2008, 130, 1833-1835. (b) Chen, B.; Ockwig, N. W.; Millard, A. R.; Contreras, D. S.; Yaghi, O. M. *Angew. Chem. Int. Ed.* 2005, 44, 4745-4749. (c) Dinca, M.; Dailly, A.; Liu, Y.; Brown, C. M.; Neumann, D. A.; Long, J. R. *J. Am. Chem. Soc.* 2006, 128, 16876-16883. (d) Latroche, M.; Surblé, S.; Serre, C.; Mellot-Draznieks, C.; Llewellyn, P. L.; Lee, H.; Chang, J.; Jhung, S. H.; Férey, G. *Angew. Chem., Int. Ed.* 2006, 45, 8227-8231. (e) Mulfort, K. L.; Hupp, J. T. *J. Am. Chem. Soc.* 2007, 129, 9604-9605. (f) Farha, O. K.; Spokoyny, A. M.; Mulfort, K. L.; Hawthorne, M. F.; Mirkin, C. A.; Hupp, J. T. *J. Am. Chem. Soc.* 2007, 129, 12680-12680.
5. Rieter, W. J.; Taylor, K. M. L.; An, H.; Lin, W.; Lin, W. *J. Am. Chem. Soc.*, 2006, 128, 9024-9025.
6. Horcajada, P.; Serre, C.; Vallet-Regí, M.; Sebban, M.; Taulelle, F.; Férey, G. *Angew. Chem., Int. Ed.* 2006, 118, 6120.
7. Eddaoudi, M.; Kim, J.; Rosi, N.; Vodak, D.; Wachter, J.; O'Keeffe, M.; Yaghi, O. M. *Science*, 2002, 295, 469-472.
8. See, for example: Gadzikwa, T.; Zeng, B-S.; Hupp, J. T.; Nguyen, S. T. *Chem. Commun.*, 2008, 3672-3674.

9. For example, compound 8 (below) degrades under solvothermal conditions (likely by polymerization), preventing MOF formation.
10. (a) Wang, Z.; Cohen, S. M. *J. Am. Chem. Soc.* 2007, 129, 12368-12369. (b) Wang, Z.; Cohen, S. M. *Angew. Chem., Int. Ed.* 2008, 47, 4699-4702. (c) Tanabe, K. K.; Wang, Z.; Cohen, S. M. *J. Am. Chem. Soc.* 2008, 130, 8508-8517. (d) Seo, J. S.; Whang, D.; Lee, H.; Jun, S. I.; Oh, J.; Jeon, Y. J.; Kim, K. *Nature* 2000, 404, 982-986. (e) Kaye, S. S.; Long, J. R. *J. Am. Chem. Soc.* 2007, 130, 806-807. (f) Gadzikwa, T.; Lu, G.; Stern, C. L.; Wilson, S. R.; Hupp, J. T.; Nguyen, S. T. *Chem. Commun.* 2008, in press (DOI:10.1039/b805101a) (g) Mulfort, K. L.; Hupp, J. T. *Inorg. Chem.* 2008, 47, 7936-7938. (h) Chuii, S. S. Y.; Lo, S. M. F.; Charmant, J. P. H.; Orpen, A. G.; Williams, I. D. *Science*, 1999, 283, 1148-1150.
11. (a) Han, S. S.; Goddard, W. A., III, *J. Am. Chem. Soc.* 2007, 129, 8422-8423. (b) Blomqvist, A.; Araujo, C. M.; Srepusharawoot, P.; Ahuja, R., *Proc. Natl. Acad. Sci. U.S.A.* 2007, 104, 20173-20176. (c) Dalach, P.; Frost, H.; Snurr, R. Q.; Ellis, D. E., *J. Phys. Chem. C* 2008, 112, 9278-9284. (d) Mavrandonakis, A.; Tylianakis, E.; Stubos, A. K.; Froudakis, G. E., *J. Phys. Chem. C* 2008, 112, 7290-7294.
12. Cho, S., -H.; Gadzikwa, T.; Emberger, G. A.; Snurr, R. Q.; Nguyen, S. T.; Hupp, J. T. *PMSE Preprints,* 2007, 97, 95-96.
13. Kolb, H. C., Finn, M. G.; Sharpless, K. B. *Angew. Chem. Int. Ed.,* 2001, 40, 2004-2021.
14. An exception is the early work of Chui and co-workers (ref. 10h). They report that [Cu₃(benzne-1,3,5-carboxylate)₃(H₂O)₃]$_n$ (also known as "HKUST-1") can be derivatized with pyridine via displacement of water. While likely correct, the evidence for derivatization is limited—consisting of elemental analysis data showing incorporation of 1.5 pyridines per Cu and interpreted as uptake of both coordinated and non-coordinated pyridine. Selective removal of non-coordinated pyridine was not reported, possibly because of the relatively low temperature for decomposition of the parent compound (240° C.). Properties of the putative modified cavity (e.g. surface area, micropore volume, sorbate uptake) were not explored.
15. Hwang, Y. K.; Hong, D-Y; Chang, J-S; Jhung, S. H.; Seo, Y-K; Kim, J.; Vimont, A.; Daturi, M.; Serre, C.; Férey. G. 2008, 47, 4144-4148.
16. See, for example: (a) Chen, B.; Ockwig, N. W.; Millward, A. R.; Contreras, D. S.; Yaghi, O. M. *Angew. Chem., Int. Ed.* 2005, 30, 4745-4749. (b) Dinca, M.; Dailly, A.; Liu, Y.; Brown, C. M.; Neumann, D. A.; Jeffrey R. Long, J. R. *J. Am. Chem. Soc.,* 2006, 128, 16876-16883.
17. Spek, A. L. *J. Appl. Crystallogr.* 2003, 36, 7-13. The PLATON analyses were performed by using data collected for 3.
18. For an up-to-date survey, see: Zhao, D.; Yuan, D.; Zhou, H-C. *Energy Environ. Sci.,* 2008, DOI: 10.1039/b808322n.
19. Frost, H.; Duren, T.; Snurr, R. Q. *J. Phys. Chem. B* 2006, 110, 9565-9570.
20. R. Babarao, Z. Q. Hu, J. W. Jiang, S. Chempath and S. I. Sandler, *Langmuir,* 2007, 23, 659; S. R. Challa, D. S. Sholl and J. K. Johnson, *J. Chem. Phys.,* 2002, 116, 814; A. Goj, D. S. Sholl, E. D. Akten and D. Kohen, *J. Phys. Chem. B,* 2002, 106, 8367; Q. Y. Yang and C. L. Zhong, *J. Phys. Chem. B,* 2006, 110, 17776; Y.-S. Bae, K. L. Mulfort, H. Frost, P. Ryan, S. Punnathanam, L. J. Broadbelt, J. T. Hupp and R. Q. Snurr, *Langmuir,* 2008, 24, 8592.
21. Q. Yang, C. Xue, C. Zhong and J.-F. Chen, *AIChE J.,* 2007, 53, 2832.

We claim:

1. A compound selected from compounds of a formula

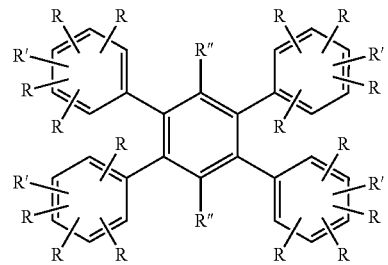

and compounds of a formula

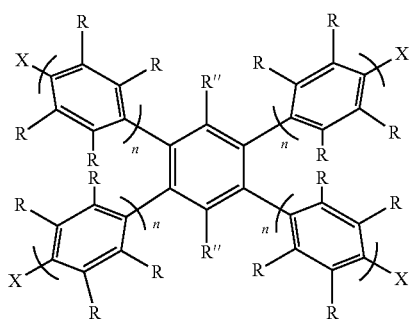

wherein
X is

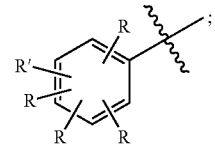

R' at each instance is —COOH;
R at each instance is independently selected from H, F, Br, I and $CH_3$;
R" at each instance is independently selected from H, F, Br, I and $CH_3$; and
n is an integer selected from 1 and integers greater than 1, and salts thereof.

2. The compound according to claim 1 wherein each R is H and each R" is H.

3. A metal-organic framework comprising a compound according to claim 1, and a metal, the metal-organic framework being robust, non-catenated, 3 dimensional, and permanently microporous.

4. The metal-organic framework building block of claim 3 wherein the metal comprises a Zn(II) ion.

5. The metal-organic framework building block of claim 4 having a formula $[Zn_2(A)(B)_2]_n$, wherein A is a compound of claim 1, n is about 22 to about 100 and B is nothing or selected from R'''-pyridin-4-yl and DMF, where R''' is selected from H, methyl, ethyl, ethenyl and $CF_3$.

6. The metal-organic framework of claim 5 wherein B is R'''-pyridin-4-yl and R''' is selected from H, methyl, ethyl, ethenyl and $CF_3$.

7. A gas adsorption separation process characterized by selectively removing one or more gases from a gas mixture by contacting the gas mixture with a metal-organic framework of claim 5.

8. The gas adsorption separation process of claim 7 wherein $CO_2$ is selectively removed from the gas mixture.

9. The gas adsorption separation process of claim 8 wherein B of the metal-organic framework is R'''-pyridin-4-yl and R''' is selected from H, methyl, ethyl, ethenyl and $CF_3$.

10. The gas adsorption separation process of claim 9 wherein R''' is $CF_3$.

11. The metal-organic framework of claim 3 wherein the compound is of the formula

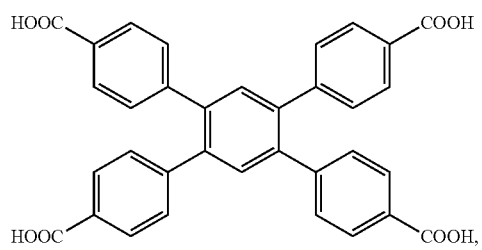 [SMILES: O=C(O)c1ccc(-c2cc(-c3ccc(C(=O)O)cc3)c(-c3ccc(C(=O)O)cc3)cc2-c2ccc(C(=O)O)cc2)cc1]

the metal-organic framework comprising a compound of the formula

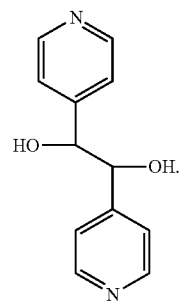

12. The metal-organic framework of claim 3 wherein the compound is of the formula

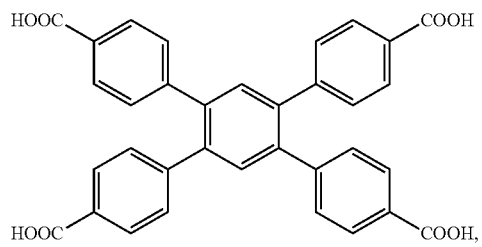

the metal-organic framework comprising a compound of the formula

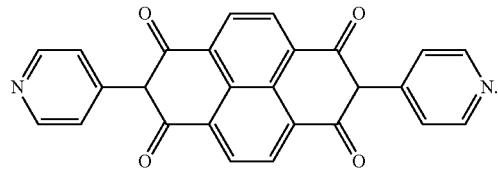 [SMILES: O=C1c2ccc3c4c(ccc(c24)C(=O)C1c1ccncc1)C(=O)C(c1ccncc1)C3=O]

13. The metal-organic framework of claim 3 wherein the compound is of the formula

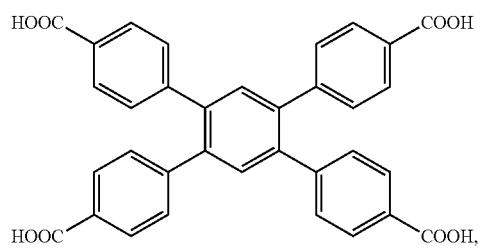 [SMILES: O=C(O)c1ccc(-c2cc(-c3ccc(C(=O)O)cc3)c(-c3ccc(C(=O)O)cc3)cc2-c2ccc(C(=O)O)cc2)cc1]

the metal-organic framework comprising a compound of the formula

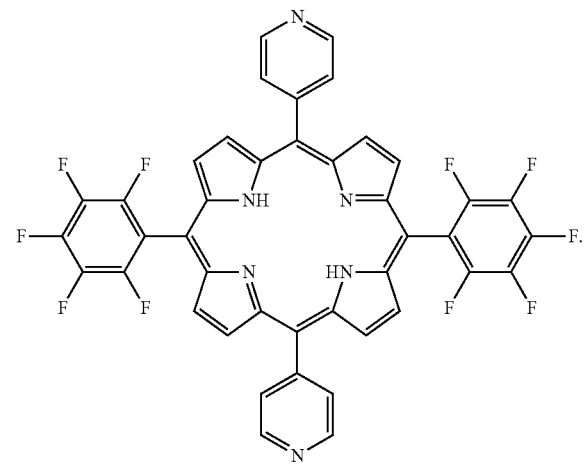 [SMILES: Fc1c(F)c(F)c(-c2c3nc(c(-c4ccncc4)c4ccc([nH]4)c(-c4c(F)c(F)c(F)c(F)c4F)c4nc(c(-c5ccncc5)c5ccc2[nH]5)C=C4)C=C3)c(F)c1F]

* * * * *